(12) United States Patent
Wallweber

(10) Patent No.: US 10,451,614 B2
(45) Date of Patent: Oct. 22, 2019

(54) METHODS OF ASSESSING PROTEIN INTERACTIONS BETWEEN CELLS

(71) Applicant: LABORATORY CORPORATION OF AMERICA HOLDINGS, Burlington, NC (US)

(72) Inventor: Gerald J. Wallweber, Foster City, CA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 0 days.

(21) Appl. No.: 16/080,428

(22) PCT Filed: Mar. 15, 2017

(86) PCT No.: PCT/US2017/022566
§ 371 (c)(1),
(2) Date: Aug. 28, 2018

(87) PCT Pub. No.: WO2017/161030
PCT Pub. Date: Sep. 21, 2017

(65) Prior Publication Data
US 2019/0064156 A1    Feb. 28, 2019

Related U.S. Application Data

(60) Provisional application No. 62/308,587, filed on Mar. 15, 2016.

(51) Int. Cl.
| | |
|---|---|
| *G01N 31/00* | (2006.01) |
| *G01N 33/53* | (2006.01) |
| *G01N 33/542* | (2006.01) |
| *G01N 33/574* | (2006.01) |
| *G01N 33/68* | (2006.01) |

(52) U.S. Cl.
CPC ......... *G01N 33/542* (2013.01); *G01N 33/574* (2013.01); *G01N 33/57488* (2013.01); *G01N 33/57492* (2013.01); *G01N 33/6845* (2013.01); *G01N 2500/02* (2013.01); *G01N 2500/10* (2013.01); *G01N 2800/52* (2013.01)

(58) Field of Classification Search
None
See application file for complete search history.

(56) References Cited

U.S. PATENT DOCUMENTS

| | | |
|---|---|---|
| 6,322,980 B1 | 11/2001 | Singh |
| 6,514,700 B1 | 2/2003 | Singh |
| 6,627,400 B1 | 9/2003 | Singh et al. |
| 6,630,296 B2 | 10/2003 | Xue et al. |
| 6,649,351 B2 | 11/2003 | Matray et al. |
| 6,673,550 B2 | 1/2004 | Matray et al. |
| 6,682,887 B1 | 1/2004 | Singh |
| 6,686,152 B2 | 2/2004 | Singh et al. |
| 6,770,439 B2 | 8/2004 | Singh et al. |
| 6,818,399 B2 | 11/2004 | Singh et al. |
| 6,846,645 B2 | 1/2005 | Xue et al. |
| 6,916,612 B2 | 7/2005 | Singh et al. |
| 6,949,347 B2 | 9/2005 | Singh et al. |
| 6,955,874 B2 | 10/2005 | Singh et al. |
| 7,001,725 B2 | 2/2006 | Singh et al. |
| 7,037,654 B2 | 5/2006 | Chenna et al. |
| 7,041,459 B2 | 5/2006 | Singh et al. |
| 7,045,311 B2 | 5/2006 | Ciambrone et al. |
| 7,105,308 B2 | 9/2006 | Chan-Hui et al. |
| 7,135,300 B2 | 11/2006 | Chan-Hui et al. |
| 7,160,735 B2 | 1/2007 | Dehlinger et al. |
| 7,217,531 B2 | 5/2007 | Singh et al. |
| 7,255,999 B2 | 8/2007 | Singh et al. |
| 7,279,585 B2 | 10/2007 | Singh et al. |
| 7,312,034 B2 | 12/2007 | Virgos et al. |
| 7,358,052 B2 | 4/2008 | Singh |
| 7,402,397 B2 | 7/2008 | Chan-Hui et al. |
| 7,402,398 B2 | 7/2008 | Pidaparthi et al. |

(Continued)

FOREIGN PATENT DOCUMENTS

| | | |
|---|---|---|
| EP | 3156484 A1 | 4/2017 |
| WO | WO 00/66607 | 11/2000 |

(Continued)

OTHER PUBLICATIONS

Huang et al. ["Comparison of central HER-2 expression and HER2 homodimer using a novel proximity based assay", American College of Pathologist (CAP) Annual Meeting, Sep. 25-28, 2008 (Poster 40)].*
Eli et al. Intl. Conference on Molecular Targets and Cancer Therapeutics, AACR-NCI-EORTC, Oct. 21-24, 2008, Geneva Switzerland (Poster 88).*
Tascilar et al. (Annals of Oncology 10,Suppl. 4:S107-S110, 1999).*
Tockman et al. (Cancer Research 52:2711s-2718s, 1992).*
Biernat, W. et al., "Quantitative HER2 levels and steroid receptor expression in primary breast cancers and in matched brain metastases," 2012 J. Clin. Oncol. 30 (Jun. 20 Suppl.): Abstract 603.
Biernat, W. et al., "Quantitative HER2 levels and steroid receptor expression in primary breast cancers and in matched brain metastases," 35th Annual American Society of Clinical Oncology (ASCO) Conference, May 31-Jun. 4, 2012; Chicago, IL (Poster 603).

(Continued)

*Primary Examiner* — Lisa V Cook
(74) *Attorney, Agent, or Firm* — Kilpatrick Townsend & Stockton LLP

(57) ABSTRACT

Provided are methods of detecting and quantitatively measuring protein-protein interactions between proteins present on the surface of different cells using a sensitive antibody based assay. Antibodies specific for each target protein are either directly labeled, or are detected by labeled secondary antibodies. The antibodies are labeled with detectable tags that are releasable when the target proteins are within proximity to each other. Also provided are methods for facilitating diagnosis, prognosis, and treatment of cancer using this assay to detect protein-protein interactions between target proteins of interest. Methods of screening test agents that impact the protein-protein interaction are also provided.

17 Claims, 13 Drawing Sheets

(56) References Cited

U.S. PATENT DOCUMENTS

| | | |
|---|---|---|
| 7,402,399 B2 | 7/2008 | Mukherjee et al. |
| 7,537,938 B2 | 5/2009 | Kirakossian et al. |
| 7,648,828 B2 | 1/2010 | Chan-Hui et al. |
| 7,771,929 B2 | 8/2010 | Singh et al. |
| 7,939,267 B2 | 5/2011 | Moore et al. |
| 8,198,031 B2 | 6/2012 | Chan-Yui et al. |
| 8,247,180 B2 | 8/2012 | Pidaparthi et al. |
| 8,349,574 B2 | 1/2013 | Bates et al. |
| 8,357,277 B2 | 1/2013 | Badal et al. |
| 8,470,542 B2 | 6/2013 | Sperinde et al. |
| RE44,437 E | 8/2013 | Chan-Hui et al. |
| 9,081,019 B2 | 7/2015 | Sperinde et al. |
| 9,110,066 B2 | 8/2015 | Bates et al. |
| 9,110,075 B2 | 8/2015 | Singh et al. |
| 9,766,242 B2 | 9/2017 | Bates et al. |
| 9,939,447 B2 | 4/2018 | Singh et al. |
| 2002/0045738 A1 | 4/2002 | Singh et al. |
| 2002/0058263 A1 | 5/2002 | Singh et al. |
| 2003/0092012 A1 | 5/2003 | Chenna et al. |
| 2003/0170734 A1 | 9/2003 | Williams et al. |
| 2003/0175747 A1 | 9/2003 | Singh |
| 2003/0203408 A1 | 10/2003 | Williams et al. |
| 2003/0207300 A1 | 11/2003 | Matray et al. |
| 2003/0235832 A1 | 12/2003 | Chenna et al. |
| 2004/0029139 A1 | 2/2004 | Singh |
| 2004/0067498 A1 | 4/2004 | Chenna et al. |
| 2004/0091850 A1 | 5/2004 | Boone et al. |
| 2004/0166529 A1 | 8/2004 | Singh et al. |
| 2004/0175765 A1 | 9/2004 | Singh et al. |
| 2004/0197815 A1 | 10/2004 | Singh et al. |
| 2004/0229293 A1 | 11/2004 | Chan-Hui et al. |
| 2004/0229294 A1 | 11/2004 | Chan-Hui et al. |
| 2004/0229299 A1 | 11/2004 | Badal et al. |
| 2004/0229380 A1 | 11/2004 | Chan-Hui et al. |
| 2004/0248150 A1 | 12/2004 | Singh et al. |
| 2004/0265858 A1 | 12/2004 | Singh et al. |
| 2005/0048553 A1 | 3/2005 | Chenna et al. |
| 2005/0130238 A1 | 6/2005 | Chan-Hui et al. |
| 2005/0130246 A1 | 6/2005 | Salimi-Moosavi et al. |
| 2005/0170438 A1 | 8/2005 | Chan-Hui et al. |
| 2006/0199231 A1 | 9/2006 | Moore et al. |
| 2006/0223107 A1 | 10/2006 | Chenna et al. |
| 2008/0187948 A1 | 8/2008 | Chan-Hui et al. |
| 2008/0233602 A1 | 9/2008 | Chan-Hui et al. |
| 2008/0254497 A1 | 10/2008 | Singh |
| 2008/0311674 A1 | 12/2008 | Singh et al. |
| 2009/0011432 A1 | 1/2009 | Chan-Hui et al. |
| 2009/0011440 A1 | 1/2009 | Mukherjee et al. |
| 2009/0111127 A1 | 4/2009 | Chan-Hui et al. |
| 2009/0155818 A1 | 6/2009 | Pidaparthi et al. |
| 2009/0173631 A1 | 7/2009 | Boone et al. |
| 2009/0191559 A1 | 7/2009 | Huang et al. |
| 2010/0143927 A1 | 6/2010 | Sperinde et al. |
| 2010/0210334 A1 | 8/2010 | Bates et al. |
| 2010/0233732 A1 | 9/2010 | Bates et al. |
| 2010/0291594 A1 | 11/2010 | Chan-Hui et al. |
| 2011/0180408 A1 | 7/2011 | Badal et al. |
| 2012/0295259 A1 | 11/2012 | Huang et al. |
| 2013/0216523 A1 | 8/2013 | Wallweber |
| 2015/0376293 A1 | 12/2015 | Sperinde |
| 2016/0041171 A1 | 2/2016 | Wallweber |
| 2018/0164319 A1 | 6/2018 | Bates et al. |

FOREIGN PATENT DOCUMENTS

| | | |
|---|---|---|
| WO | WO 01/83502 | 11/2001 |
| WO | WO 02/12547 | 2/2002 |
| WO | WO 02/94998 | 11/2002 |
| WO | WO 02/95356 | 11/2002 |
| WO | WO 03/006947 | 1/2003 |
| WO | WO 03/033741 | 4/2003 |
| WO | WO 03/042398 | 5/2003 |
| WO | WO 03/042657 | 5/2003 |
| WO | WO 03/042658 | 5/2003 |
| WO | WO 03/042699 | 5/2003 |
| WO | WO 03/076649 | 9/2003 |
| WO | WO 03/085374 | 10/2003 |
| WO | WO 04/010842 | 2/2004 |
| WO | WO 04/011900 | 2/2004 |
| WO | WO 04/061131 | 7/2004 |
| WO | WO 04/061446 | 7/2004 |
| WO | WO 04/063700 | 7/2004 |
| WO | WO 04/068116 | 8/2004 |
| WO | WO 04/087887 | 10/2004 |
| WO | WO 04/091384 | 10/2004 |
| WO | WO 04/092353 | 10/2004 |
| WO | WO 05/019470 | 3/2005 |
| WO | WO 05/037071 | 4/2005 |
| WO | WO 05/045058 | 5/2005 |
| WO | WO 05/072507 | 8/2005 |
| WO | WO 06/044748 | 4/2006 |
| WO | WO 06/052788 | 5/2006 |
| WO | WO 06/084018 | 8/2006 |
| WO | WO 07/021317 | 2/2007 |
| WO | WO 09/070772 | 6/2009 |
| WO | WO 09/086197 | 7/2009 |
| WO | WO 10/065568 | 6/2010 |
| WO | WO 10/083463 | 7/2010 |
| WO | WO 10/083470 | 7/2010 |
| WO | WO 12/159115 | 11/2012 |
| WO | 2014124046 | 8/2014 |
| WO | WO 14/165855 | 10/2014 |
| WO | 2015038799 | 3/2015 |
| WO | WO 2015/190529 A1 | 12/2015 |
| WO | WO 2017/161030 | 9/2017 |

OTHER PUBLICATIONS

Huang, W. et al., "Quantitative HER2 measurement and PI3K mutation profile in matched primary and metastatic breast cancer tissues," 2012 J. Clin. Oncol. 30 (Jun. 20 Suppl.): Abstract 614.

Huang, W. et al., "Quantitative HER2 measurement and PI3K mutation profile in matched primary and metastatic breast cancer tissues," 35th Annual American Society of Clinical Oncology (ASCO) Conference, May 31-Jun. 4, 2012, Chicago, IL (Poster 614).

Sperinde, J. et al., "A comparative study of p95-HER2 carboxy terminal fragment (CTF) detected by immunohistochemistry and VeraTag immunoassays in human breast tumors," In: Proc. Am. Assoc. Cancer Res., Mar. 31, 2012-Apr. 4, 2012, Chicago, IL. Philadelphia (PA): AACR; Cancer Res. 2012, 72(8 Suppl): Abstract 687.

Sperinde, J. et al., "A comparative study of p95-HER2 carboxy terminal fragment (CTF) detected by immunohistochemistry and VeraTag immunoassays in human breast tumors," 103rd Annual American Association for Cancer Research (AACR) Conference, Mar. 31-Apr. 4, 2012, Chicago, IL (Poster 687).

Villasboas, J.C. et al., "Correlation of quantitative p95HER2, HER3, and HER2 protein expression with pathologic complete response (pCR) in HER2-positive breast cancer patients treated with neoadjuvant (NEO) trastuzumab containing therapy," 2012 J. Clin. Oncol. 30 (Jun. 20 Suppl.): Abstract 608.

Villasboas, J.C. et al., "Correlation of quantitative p95HER2, HER3, and HER2 protein expression with pathologic complete response (pCR) in HER2-positive breast cancer patients treated with neoadjuvant (NEO) trastuzumab containing therapy," 35th Annual American Society of Clinical Oncology (ASCO) Conference, May 31-Jun. 4, 2012, Chicago, IL (Poster 608).

Biernat, W. et al., "Quantitative measurements of p95HER2 (p95) and total HER2 (H2T) protein expression in patients with trastuzumab-treated, metastatic breast cancer (MBC): Independent confirmation of clinical cutoffs," 2011 J. Clin. Oncol. 29(15)(May 20 Suppl.): Abstract 586.

Biernat, W. et al., "Quantitative measurements of p95HER2 (p95) and total HER2 (H2T) protein expression in patients with trastuzumab-treated, metastatic breast cancer (MBC): Independent confirmation of clinical cutoffs," American Society of Clinical Oncology (ASCO) Annual Meeting, Jun. 3-7, 2011, Chicago, IL (Poster 586).

(56) References Cited

OTHER PUBLICATIONS

Cook, J.W. et al., "Mutations in the catalytic domain of PI3 kinase and correlation with clinical outcome in trastuzumab-treated metastatic breast cancer (MBC)," 2011 J. Clin. Oncol. 29(15)(May 20 Suppl.): Abstract 582.

Cook, J.W. et al., "Mutations in the catalytic domain of PI3 kinase and correlation with clinical outcome in trastuzumab-treated metastatic breast cancer (MBC)," American Society of Clinical Oncology (ASCO) Annual Meeting, Jun. 3-7, 2011, Chicago, IL (Poster 582).

Duchnowska, R. et al., "Correlation between Quantitative HER2 Protein Expression and Risk of Brain Metastases in HER2-Positive Advanced Breast Cancer Patients Receiving Trastuzumab-Containing Therapy," Cancer Research, Dec. 15, 2011, 71(24 Suppl. 3):291s (Abstract P2-12-05).

Duchnowska, R. et al., "Correlation between Quantitative HER2 Protein Expression and Risk of Brain Metastases in HER2-Positive Advanced Breast Cancer Patients Receiving Trastuzumab-Containing Therapy," 34th Annual San Antonio Breast Cancer Symposium, Dec. 6-10, 2011, San Antonio, TX, USA (Poster P2-12-05).

Huang, W. et al., "Comparison of four HER2 testing methods in detection of HER2-positive breast cancer: results in the FinHer study cohort," Cancer Research, Dec. 15, 2011, 71(24)(Suppl. 3):187s-188s (Abstract P1-07-01).

Huang, W. et al., "Comparison of four HER2 testing methods in detection of HER2-positive breast cancer: results in the FinHer study cohort," Annual San Antonio Breast Cancer Symposium, Dec. 6-10, 2011, San Antonio, TX, USA (Poster P1-07-01).

Huang, W. et al., "Assessment of real-world HER2 status by immunohistochemistry (IHC) and fluorescence in situ hybridization (FISH) in breast cancers: Comparison with HERMark®, a validated quantitative measure of HER2 protein expression," Cancer Research, Dec. 15, 2011, 71(24)(Suppl. 3):192s-193s (Abstract P1-07-12).

Huang, W. et al., "Assessment of real-world HER2 status by immunohistochemistry (IHC) and fluorescence in situ hybridization (FISH) in breast cancers: Comparison with HERMark®, a validated quantitative measure of HER2 protein expression," Annual San Antonio Breast Cancer Symposium, Dec. 6-10, 2011, San Antonio, TX, USA (Poster P1-07-12).

Shi, Y. et al., "Quantitative measurement of HER3-PI3K complex and total p85α subunit in formalin-fixed, paraffin-embedded (FFPE) tissues using VeraTagTM immunoassays," American Association for Cancer Research Special Conference: Targeting PI3K/mTOR Signaling in Cancer, Feb. 24-27, 2011, San Francisco, CA: Poster.

Wallweber, J. et al., "Subclassification of squamous cell carcinomas of the head and neck based on HER/ErbB and c-Met receptor protein expression and activation profiles," In: Proc. Am. Assoc. Cancer Res. AACR, Apr. 2-6, 2011, Orlando, FL: Abstract LB-323.

Wallweber, J. et al., "Subclassification of squamous cell carcinomas of the head and neck based on HER/ErbB and c-MET receptor protein expression and activation profiles," 102nd Annual American Association of Cancer Research (AACR) Conference, Apr. 2-6, 2011, Orlando, FL (Poster LB-323).

Duchnowska, R. et al., "Correlation between quantitative HER2 Protein level and the risk of brain metastases (BM) in patients (ots) with metastatic breast cancer (MBC) treated with trastuzumab-containing therapy," 2010 J. Clin. Oncol. 28(15s) (Jun. 20 Suppl.): Abstract 1030.

Duchnowska, R. et al., "Correlation between quantitative HER2 Protein level and the risk of brain metastases (BM) in patients (ots) with metastatic breast cancer (MBC) treated with trastuzumab-containing therapy," 33rd Annual American Society of Clinical Oncology (ASCO) Conference, Jun. 4-8, 2010, Chicago, IL (Poster 1030).

Wallweber, J., "Quantitative assessment of HER/erbB receptor protein expression and activation status in FFPE tumor samples identifies an activated HER1 signature in squamous cell carcinomas of the head and neck," In: Proc. Am. Assoc. Cancer Res. AACR, Apr. 17-21, 2010, Washington, D.C.: Abstract LB-66.

Wallweber, J., "Quantitative assessment of HER/erbB receptor protein expression and activation status in FFPE tumor samples identifies an activated HER1 signature in squamous cell carcinomas of the head and neck," 101st Annual American Association of Cancer Research (AACR) Conference, Apr. 17-21, 2010, Washington, D.C. (Poster LB-66).

Bates, M. et al., "Relationship between Quantitative HER2 Protein Expression and Clinical Outcomes in ER-Positive and ER-Negative Sub-Groups of Patients with Trastuzumab," Dec. 15, 2009, Cancer Research 69(24)(Suppl. 1): Abstract 5136.

Bates, M. et al., "Relationship between Quantitative HER2 Protein Expression and Clinical Outcomes in ER-Positive and ER-Negative Sub-Groups of Patients with Trastuzumab," 32nd Annual San Antonio Breast Cancer Symposium, Dec. 9-13, 2009, San Antonio, TX, USA (Poster 5136).

Eli, L. et al., "Quantitative measurements of phosphorylated HER1, HER2, and HER1-HER2 heterodimers in formalin-fixed, paraffin-embedded (FFPE) breast and head/neck tumors using proximity-based immunoassays," In: Proc. Am. Assoc. Cancer Res. AACR, Apr. 18-22, 2009, Denver, CO: Abstract 5247.

Eli, L. et al., "Quantitative measurements of phosphorylated HER1, HER2, and HER1-HER2 heterodimers in formalin-fixed, paraffin-embedded (FFPE) breast and head/neck tumors using proximity-based immunoassays," 100th Annual American Association of Cancer Research (AACR) Conference, Apr. 18-22, 2009, Denver, CO (Poster 5247).

Joensuu, H. et al. "Breast cancer patients with very high tumor HER2 expression levels might not benefit from treatment with trastuzumab plus chemotherapy: A retrospective exploratory analysis of the FinHer trial," Dec. 15, 2009, Cancer Research 69(24)(Suppl. 1): Abstract 5083.

Joensuu, H. et al. "Breast cancer patients with very high tumor HER2 expression levels might not benefit from treatment with trastuzumab plus chemotherapy: A retrospective exploratory analysis of the FinHer trial," 32nd Annual San Antonio Breast Cancer Symposium, Dec. 10-13, 2009, San Antonio, TX, USA.

Leitzel, A. et al., "Discordant HER2 Total and HER2 Homodimer Levels by HERmark Analysis in Matched Primary and Metastatic Breast Cancer FFPE Specimens," Cancer Research, Dec. 15, 2009, 69(24 Suppl. 3): Abstract 2131.

Leitzel, A. et al., "Discordant HER2 Total and HER2 Homodimer Levels by HERmark Analysis in Matched Primary and Metastatic Breast Cancer FFPE Specimens," 32nd Annual San Antonio Breast Cancer Symposium, Dec. 9-13, 2009, San Antonio, TX, USA (Poster 2132).

Lipton, A. et al., "Multiple Subtypes of HER-2/Neu-Positive Metastatic Breast Cancer," Cancer Research, Dec. 15, 2009, 69(24 Suppl. 3): Abstract 20.

Lipton, A. et al., "Multiple Subtypes of HER-2/Neu-Positive Metastatic Breast Cancer," 32nd Annual San Antonio Breast Cancer Symposium, Dec. 9-13, 2009, San Antonio, TX, USA (Poster 2030).

Shi, Y. et al., "Quantitative, sensitive, and reproducible measurement of epidermal growth factor receptor/HER1 homodimerization and total expression in formalin-fixed, paraffin-embedded tumors using a novel proximity-based assay," In: Proc. Am. Assoc. Cancer Res. AACR, Apr. 18-22, 2009, Denver, CO: Abstract 5244.

Shi, Y. et al., "Quantitative, sensitive, and reproducible measurement of epidermal growth factor receptor/HER1 homodimerization and total expression in formalin-fixed, paraffin-embedded tumors using a novel proximity-based assay," 100th Annual American Association for Cancer Research (AACR) Conference, Apr. 18-22, 2009 Denver, CO (Poster 5244).

Shi, Y. et al., "Multiplexed assay for assessing ErbB/HER receptor pathways in formalin-fixed and paraffin-embedded cancer cell lines," In: Proc. Am. Assoc. Cancer Res. AACR, Apr. 18-22, 2009, Denver, CO: Abstract 5762.

Williams, S. et al., "Profiling PI3K-Akt pathway activation in formalin fixed, paraffin-embedded cell line models and breast and ovarian tumors using a novel proximity assay," In: Proc. Am. Assoc. Cancer Res. AACR, Apr. 18-22, 2009, Denver, CO: Abstract 5251.

Williams, S. et al., "Profiling PI3K-Akt pathway activation in formalin fixed, paraffin-embedded cell line models and breast and ovarian tumors using a novel proximity assay," 100th Annual

(56) References Cited

OTHER PUBLICATIONS

American Association of Cancer Research (AACR) Conference, Apr. 18-22, 2009, Denver, CO (Poster 5251).

Amler, L. et al., "Downregulation of HER3 may predict clinical benefit in ovarian cancer from pertuzumab, a HER2 dimerization-inhibiting antibody," 2008, Molecular Markers Meeting, Amer. Soc. Clin. Onc., Abstract 25.

Badal, M.Y. et al., "Measurement of the HER3-PI3K complex as a marker of PI3K-Akt pathway activation in formalin fixed, paraffin-embedded cell line models and breast and ovarian tumors using a novel proximity assay," American Association for Cancer Research (AACR) Special Conference on Targeting the PI3K-Kinase Pathway in Cancer, Nov. 11-14, 2008, Cambridge, MA, USA (Poster).

Bates, M., et al., "Quantitative HER2 homodimer levels correlate with time to first recurrence in HER2-positive breast cancer patients who did not receive trastuzumab in the adjuvant setting," Cancer Res. Jan. 15, 2009, 69(2 Suppl. 1): Abstract 1074.

Bates, M. et al., "Quantitative HER2 homodimer levels correlate with time to first recurrence in HER2-positive breast cancer patients who did not receive trastuzumab in the adjuvant setting," 31st Annual San Antonio Breast Cancer Symposium, Dec. 10-14, 2008, San Antonio, TX, USA (Poster 1074).

Eli, L. et al., "Development of novel-proximity-based immunoassays for activated HER1, HER2, HER1-HER2 heterodimers in formalin-fixed, paraffin-embedded (FFPE) cells," 2008 Eur. J. Cancer 6(Oct. 12):30 (Abstract 88).

Eli, L. et al., "Development of novel-proximity-based immunoassays for activated HER1, HER2, HER1-HER2 heterodimers in formalin-fixed, paraffin-embedded (FFPE) cells," Intl. Conference on Molecular Targets and Cancer Therapeutics, AACR-NCI-EORTC, Oct. 21-24, 2008, Geneva, Switzerland (Poster 88).

Huang, W. et al., "Comparison of Central HER-2 Tests With Quantitative HER-2 Expression and HER-2 Homodimer Measurements Using a Novel Proximity Based Assay," 2008 Arch. Pathol. Lab. Med. 132 (Sep.):1476 (CAP Abstract 40).

Huang, W. et al., "Comparison of Central HER-2 Tests With Quantitative HER-2 Expression and HER-2 Homodimer Measurements Using a Novel Proximity Based Assay," American College of Pathologist (CAP) Annual Meeting, Sep. 25-28, 2008 (Poster 40).

Joensuu, H. et al., "Quantitative measurement of HER2 expression and HER2 homodimer using a novel proximity based assay: comparison with HER2 status by immunohistochemistry and chromogenic in situ hybridization in the FinHer study," Cancer Research, Jan. 15, 2009, 69(2 Suppl. 1): Abstract 2071.

Lipton, A. et al., "HER2 protein expression predicts response to trastuzumab in FISH-positive patients," Cancer Research, Jan. 15, 2009, 69(2 Suppl. 3): Abstract 32.

Lipton, A. et al., "HER2 protein expression predicts response to trastuzumab in FISH-positive patients," 31st Annual San Antonio Breast Cancer Symposium, Dec. 10-14, 2008, San Antonio, TX, USA (Poster 32).

Leitzel K., et al., "Use of total HER2 and HER2 homodimer levels to predict response to trastuzumab," J. Clin. Oncol. 2008 (May 20 Suppl.): Abstract 1002.

Leitzel, K. et al., "Total HER2 and HER2 homodimer levels predict response to trastuzumab," 44th Annual American Society of Clinical Oncology Conference, May 30-Jun. 3, 2008, Chicago, IL (Oral Presentation 1002).

Mukherjee, A. et al., "Proximity-based assays for the detection of activated HER3, HER2/3 heterodimers and HER3/PI3K complexes in FFPE cell line controls and tumors," Cancer Research, Jan. 15, 2009, 69(2 Suppl. 3): Abstract 4040.

Mukherjee, A. et al., "Proximity-based assays for the detection of activated HER3, HER2/3 heterodimers and HER3/PI3K complexes in FFPE cell line controls and tumors," 31st Annual San Antonio Breast Cancer Symposium, Dec. 10-14, 2008, San Antonio, TX, USA (Poster 4040).

Shi, Y. et al., "Development of highly quantitative, sensitive, and reproducible assays for the detection of EGFR/HER1 and ErbB3/HER3 in in formalin-fixed, paraffin-embedded cells," 2008 Eur. J. Cancer 6(Oct. 12):34-35 (Abstract 103).

Shi, Y. et al., "Development of highly quantitative, sensitive, and reproducible assays for the detection of EGFR/HER1 and ErbB3/HER3 in in formalin-fixed, paraffin-embedded cells," Intl. Conference on Molecular Targets and Cancer Therapeutics, AACR-NCI-EORTC, Oct. 21-24, 2008, Geneva, Switzerland, Poster 103.

Bates, M.P. et al., "HER2 Expression and HER2:HER2 Dimerization Identifies Subpopulations of Metastatic Breast Cancer Patients With Different Probabilities of Long-Term Survival Following Trastuzumab Treatment and With Different Requirements for Concomitant Chemotherapy," 2007 J. Clin. Oncol. 25(18S) (Jun. 20 Suppl.): Abstract 10557.

Bates, M. et al., "HER2 Expression and HER2:HER2 Dimerization Identifies Subpopulations of Metastatic Breast Cancer Patients With Different Probabilities of Long-Term Survival Following Trastuzumab Treatment and With Different Requirements for Concomitant Chemotherapy," 30th Annual American Society of Clinical Oncology (ASCO) Symposium, Jun. 1-5, 2007, Chicago, IL (Poster 10557).

Dua, R. et al., "Profiling HER-Family Receptor Dimerization in HER2 Overexpressing Cells that Coexpress Mutated EGFR Receptors," Breast Canc. Res. Treatment, Dec. 13, 2007, 106(1):5203 (Abstract 4108).

Dua, R. et al., "Profiling HER-Family Receptor Dimerization in HER2 Overexpressing Cells that Coexpress Mutated EGFR Receptors," 30th Annual San Antonio Breast Cancer Symposium, Dec. 13-16, 2007, San Antonio, TX, USA (Poster 4108).

Dua, R. et al., "Patterns of HER-Family Receptor Dimerization Intrastuzumab Susceptible and Trastuzumab Resistant Cell Lines," 2007 J. Clin. Oncol. 25(18S) (Jun. 20 Suppl.): Abstract 2533.

Dua, R. et al., "Patterns of HER-Family Receptor Dimerization Intrastuzumab Susceptible and Trastuzumab Resistant Cell Lines," 30th Annual American Society of Clinical Oncology (ASCO) Symposium, Jun. 1-5, 2007, Chicago, IL, USA (Poster 2533).

Eli, L. et al., "Development of Novel Proximity-Based Immunoassays for the Detection of HER Heterodimerization in Breast Cancer Cell Line Lysates and Formalin-Fixed, Paraffin-Embedded Tissue," Breast Cancer Research and Treatment, Dec. 13, 2007, 106(1 Suppl.):S87-S88 (Abstract 2011).

Eli, L. et al., "Development of Novel Proximity-Based Immunoassays for the Detection of HER Heterodimerization in Breast Cancer Cell Line Lysates and Formalin-Fixed, Paraffin-Embedded Tissue," 30th Annual San Antonio Breast Cancer Symposium, Dec. 13-16, 2007, San Antonio, TX, USA (Poster 2011).

Huang, W. et al., "Quantitative Measurements of HER2 Expression and HER2: HER2 Dimerization Identify Subgroups of HER2 Positive Metastatic Breast Cancer Patients with Different Probabilities of Response to Trastuzumab Treatment," Breast Can. Res. Treatment, Dec. 13, 2007, 106(1):S86 (Abstract 2007).

Huang, W. et al., "Quantitative Measurements of HER2 Expression and HER2: HER2 Dimerization Identify Subgroups of HER2 Positive Metastatic Breast Cancer Patients with Different Probabilities of Response to Trastuzumab Treatment," 30th Annual San Antonio Breast Cancer Symposium, Dec. 13-16, 2007, San Antonio, TX, USA (Poster 2007).

Shi, E. et al., "Development of Novel Proximity-Based Immunoassays for the Detection of HER Heterodimerization in Breast Cancer Cell Line Lysates and Formalin-Fixed, Paraffin-Embedded Tissue," 2007, Breast Cancer Research and Treatment, 106 (Suppl. 1) S87-S88 (Abstract).

Shi, E. et al., "Development of Novel Proximity-Based Immunoassays for the Detection of HER Heterodimerization in Breast Cancer Cell Line Lysates and Formalin-Fixed, Paraffin-Embedded Tissue," 2007, Breast Cancer Research and Treatment, 106 (Suppl. 1) S87-S88 (Poster Session II).

Toi, M. et al., "Differential Survival Following Trastuzumab Treatment Based on Quantitative HER2 Expression and HER2 Dimerization in a Clinic-Based Cohort of Patients With Metastatic Breast Cancer," 2007 J. Clin. Oncol. 25(18S) (Jun. 20 Suppl.): Abstract 1025.

Toi, M. et al., "Differential Survival following Trastuzumab Treatment based on Quantitative HER2 Expression and HER2:HER2 Dimerization in a Clinic-Based Cohort of Patients with Metastatic

(56) References Cited

OTHER PUBLICATIONS

Breast Cancer," Annual American Society of Clinical Oncology (ASCO) Conference, Jun. 1-5, 2007, Chicago, IL (Poster 1025).
Wallweber, J. et al., "Increased Detection of Breast Cancer Markers Human Epidermal Growth Factor Receptor Dimer and Downstream Signaling Proteins Utilizing the VeraTag Technology with Dextran Modified Antibodies," Breast Cancer Research and Treatment, Dec. 13, 2007, 106(1):S207 (Abstract 5002).
Wallweber, J. et al., "Increased Detection of Breast Cancer Markers Human Epidermal Growth Factor Receptor Dimer and Downstream Signaling Proteins Utilizing the VeraTag Technology with Dextran Modified Antibodies," 30th Annual San Antonio Breast Cancer Symposium, Dec. 13-16, 2007, San Antonio, TX, USA (Poster 5002).
Winslow, J. et al., "Characterization of a Novel Proximity Immunoassay for the Quantitative Determination of HER2 Protein Expression and HER2 Homodimerization in Famalin-Fixed, Paraffin-Embedded Breast Cancer Tissue," Breast Cancer Research and Treatment, Dec. 13, 2007, 106(1):S88 (Abstract 2012).
Winslow, J. et al., "Characterization of a Novel Proximity Immunoassay for the Quantitative Determination of HER2 Protein Expression and HER2 Homodimerization in Formalin-Fixed, Paraffin-Embedded Breast Cancer Tissue," 30th Annual San Antonio Breast Cancer Symposium, Dec. 13-16, 2007, San Antonio, TX, USA (Poster 2012).
Hameed, M.R. et al., "The ERB family receptor dimerization in glioblastoma—An eTag assay analysis of 23 cases," 2006 J. Clin. Oncol. 24(18S) (Jun. 20 Suppl.): Abstract 1582.
Hameed, M.R. et al., "The ERB family receptor dimerization in glioblastoma—An eTag assay analysis of 23 cases," 29th Annual American Society of Cancer Oncology (ASCO) Conference, Jun. 2-6, 2006, Atlanta, GA (Poster 1582).
Jimeno, A. et al., "Combined targeted therapy shows increased efficacy in a novel in vivo pancreas cancer model," American Association for Cancer Research (AACR) Annual Meeting, Apr. 1-6, 2006, Washington, D.C. (Abstract 2181).
Shi, Y., "Analysis of ErbB/HER receptor pathways in formalin-fixed and paraffin-embedded cancer cell lines using multiplexed eTag™ assays," 2005 J. Clin. Oncol. 23(16S) (Jun. 1 Suppl.): Abstract 9565.
Shi, Y. et al., "Analysis of ErbB/HER receptor pathways in formalin-fixed and paraffin-embedded cancer cell lines using multiplexed eTag™ assays," American Society of Clinical Oncology (ASCO) Annual Meeting, May 13-17, 2007, Orlando, FL (Poster 9565).
Dua, R. et al., "ErbB/HER pathway profiling in formalin-fixed paraffin embedded preclinical xenograft models using multiplexed proximity-based assays," Intl. Conference on Molecular Targets and Cancer Therapeutics, AACR-NCI-EORTC, Nov. 14-18, 2005, Philadelphia, PA: Abstract A121.
Dua, R. et al., "ErbB/HER pathway profiling in formalin-fixed paraffin embedded preclinical xenograft models using multiplexed proximity-based assays," Intl. Conference on Molecular Targets and Cancer Therapeutics, AACR-NCI-EORTC, Nov. 14-18, 2005, Philadelphia, PA (Poster A121).
Mukherjee, A. et al., "Correlation of ErbB activation status and clinical response in Herceptin treated breast cancer patients," 2005, Proc. Amer. Canc. Res., 46 (Apr. 16): Abstract 3688.
Mukherjee, A. et al., "Correlation of ErbB activation status and clinical response in Herceptin treated breast cancer patients," 96th Annual Meeting of the American Association for Cancer Research (AACR), Apr. 16-20, 2005, Anaheim/Orange County, CA, USA (Poster 3688).
Mukherjee, A., "The Use of ErbB/HER Activation Status as Prognostic Markers in Breast Cancer Patients Treated with Trastuzumab," 2005 J. Clin. Oncol. 23(16S) (Jun. 1 Suppl.): Abstract 553.
Mukherjee, A. et al., "The use of ErbB activation Status as Prognostic Markers in Breast Cancer Patients Treated with Trastuzumab," Amer. Society of Clin. Oncol. (ASCO) Conference May 13-17, 2005, Orlando, FL (Poster 553).
Salimi-Moosavi, H. et al., "Effect of Erbitux, Erlotinib, Gefitinib, and Rapamycin on the inhibition of EGFR dimer formation and downstream signaling pathways in different cancer cell lines," Intl. Conference on Molecular Targets and Cancer Therapeutics, AACR-NCI-EORTC, Nov. 14-18, 2005, Philadelphia, PA: Abstract A127.
Salimi-Moosavi, H. et al., "Effect of Erbitux, Erlotinib, Gefitinib, and Rapamycin on the inhibition of EGFR dimer formation and downstream signaling pathways in different cancer cell lines," Intl. Conference on Molecular Targets and Cancer Therapeutics, AACR-NCI-EORTC, Nov. 14-18, 2005, Philadelphia, PA (Poster A127).
Salimi-Moosavi, H. et al., "Effect of gefitinib on EGFR activation in lung cancer cell lines," Intl. Conference on Molecular Targets and Cancer Therapeutics, AACR-NCI-EORTC, Nov. 14-18, 2005, Philadelphia, PA: Abstract A124.
Salimi-Moosavi, H. et al., "Effect of gefitinib on EGFR activation in lung cancer cell lines," Intl. Conference on Molecular Targets and Cancer Therapeutics, AACR-NCI-EORTC, Nov. 14-18, 2005, Philadelphia, PA (Poster A124).
Salimi-Moosavi, H. et al., "IC50 determination for receptor-targeted compounds and downstream signaling," In: Proc. Am. Assoc. Cancer Res. AACR, Apr. 16-20, 2005, Anaheim, CA: Abstract 4567.
Shi, Y. et al., "Multiplexed assay for assessing ErbB/HER receptor pathways in formalin-fixed and paraffin-embedded cancer cell lines," In: Proc. Am. Assoc. Cancer Res. AACR Apr. 16-20, 2005 Anaheim, CA: Abstract 5762.
Shi, Y. et al., "Multiplexed assay for assessing ErbB/HER receptor pathways in formalin-fixed and paraffin-embedded cancer cell lines," 96th Annual American Association of Cancer Research (AACR) Conference, Apr. 16-20, 2005, Anaheim, CA (Poster 5762).
Sperinde, J. et al., "Multiplex detection of vascular endothelial growth factor receptor 2 (VEGFR2) homodimers and phosphorylation in xenografts, human tumor tissues and formalin-fixed paraffin-embedded (FFPE) samples from cell lines using the eTagTM assay system," Intl. Conference on Molecular Targets and Cancer Therapeutics, Nov. 14-18, 2005, Philadelphia, PA: Abstract B17.
Sperinde, J. et al., "Multiplex detection of vascular endothelial growth factor receptor 2 (VEGFR2) homodimers and phosphorylation in xenografts, human tumor tissues and formalin-fixed paraffin-embedded (FFPE) samples from cell lines using the eTagTM assay system," Intl. Conference on Molecular Targets and Cancer Therapeutics, Nov. 14-18, 2005, Philadelphia, PA (Poster B17).
Toi, M. et al., "The Correlation of ErbB/HER Activation Status with Breast Cancer Patient Response to Trastuzumab," National Cancer Research Cancer Institute (NCRI) Conference, Oct. 2-5, 2005, Birmingham, UK (Poster 1025).
Toi, M. et al., "The Use of ErbB/HER Activation Status as Prognostic Markers in Breast Cancer Patients Treated with Trastuzumab," American Society of Clinical Oncology (ASCO) Conference 2005, May 13th, Orlando, FL (Poster).
Yatabe, Y et al., "Application of Proximity Based Assay to Develop Algorithms That Correlate ErbB/HER Pathway Profiling and Predictive Response to EGFR/HER1 Targeted Therapy in Lung Cancer Patients," Intl. Conference on Molecular Targets and Cancer Therapeutics, Nov. 14-18, 2005, Philadelphia, PA: Abstract A123.
Yatabe, Y et al., "Application of Proximity Based Assay to Develop Algorithms That Correlate ErbB/HER Pathway Profiling and Predictive Response to EGFR/HER1 Targeted Therapy in Lung Cancer Patients," Intl. Conference on Molecular Targets and Cancer Therapeutics, Nov. 14-18, 2005, Philadelphia, PA (Poster A123).
Duchnowska, R. et al., "Correlation between quantitative HER2 protein expression and risk of brain metastasis in HER2-positive advanced breast cancer patients receiving trastuzumab-containing therapy," Oncologist 17(1):26-35 (2012) (pub. online Jan. 10, 2012).
Han, S-W, "Correlation of HER2, p95HER2 and HER3 expression and treatment outcome of lapatinib plus capecitabine in HER2-positive metastatic breast cancer," PLoS One 7(7):e39943 (2012) (pub. online Jul. 27, 2012).
Bates, M. et al., "Identification of a Subpopulation of Metastatic Breast Cancer Patients with Very High HER2 Expression Levels and Possible resistance to Trastuzumab," Ann. Oncol., 22(9):2014-2020 (2011) (pub. online Feb. 11, 2011).

(56) References Cited

OTHER PUBLICATIONS

Defazio-Eli, L. et al., "Quantitative assays for the measurement of HER1-HER2 heterodimerization and phosphorylation in cell lines and breast tumors: applications for diagnostics and targeted drug mechanism of action," Breast Canc. Res. 13:R44 (2011) (pub. Apr. 15, 2011).

Dua, R. et al., "Detection of hepatocyte growth factor (HGF) ligand-C-met receptor activation in formalin-fixed, paraffin-embedded specimens by a novel proximity assay," PLOS One 6(1): e15932 (2011) (pub. online Jan. 21, 2011).

Joensuu, H. et al., "Very high quantitative tumor HER2 content and outcome in early breast cancer," Ann. Oncol. 22(9): 2007-2013 (2011) (pub. online Feb. 1, 2011).

Ghosh, M. et al., "Trastuzumab has preferential activity against breast cancers driven by HER2 homodimers," Cancer Res. 71(5):1871 (2011) (pub. online Feb. 15, 2011).

Mukherjee, A. et al., "Profiling the HER3/PI3K Pathway in Breast Tumors Using Proximity-Directed Assays Identifies Correlations between Protein Complexes and Phosphoproteins," PLoS One 6(1): e16443 (2011) (pub. online Jan. 28, 2011).

Dua, R. et al., "EGFR over-expression and activation in high HER2, ER negative breast cancer cell lines induces trastuzumab resistance," Breast Cancer Res. Treat. 122(3):6850697 (2010) (pub. online Oct. 27, 2009).

Jain, A. et al., "HER kinase axis receptor dimer partner switching occurs in response to EGFR tyrosine kinase inhibition despite failure to block cellular proliferation," Cancer Res. 70(5):1989-1999 (2010) (pub. online Feb. 16, 2010).

Huang, Q. et al., "Comparison of central HER2 testing with quantitative total HER2 expression and HER2 homodimer measurement using a novel proximity based assay," Am. J. Clin. Pathol. 134:303-311 (2010) (pub. Aug. 2010).

Larson, J.S. et al., "Analystical validation of a highly sensitive, accurate, and reproducible assay (HERmark®) for the measurement of HER2 total protein and HER2 homodimers in FFPE breast cancer tumor specimens," Pathol. Res. Intl, 2010: Article ID 814176 (2010) (pub. online Jun. 28, 2010).

Lipton, A. et al., "Quantitative HER2 protein levels predict outcome in fluorescence in situ hybridization—positive patients with metastatic breast cancer treated with trastuzumab," Cancer 116:5168-5178 (2010) (pub. online Nov. 3, 2010).

Mamluk, R. et al., "Anti-tumor effect of CT-322 as an adnectin inhibitor of vascular endothelial growth factor receptor-2," MAbs 2(2):199-208 (2010) (pub. online Mar. 1, 2010).

Sperinde, J. et al., "Quantitation of p95HER2 in paraffin sections by using a p95-specific antibody and correlation with outcome in a cohort of trastuzumab-treated breast cancer patients," Clin. Canc. Res. 16(16):4226-4235 (2010) (pub. online Jul. 27, 2010).

Toi, M. et al., "Differential survival following trastuzumab treatment based on quantitative HER2 expression and HER2 homodimers in a clinic-based cohort of patients with metastatic breast cancer," BMC Cancer 10:56(2010) (pub. Feb. 23, 2010) (10 pages).

Desmedt, C. et al., "Quantitation of HER2 expression or HER2:HER2 dimers and differential survival in a cohort of metastatic breast cancer patients carefully selected for trastuzumab treatment primarily by FISH," Diagn. Mol. Pathol. 18(1):22-29 (2009) (pub. Mar. 2009).

Shi, Y. et al., "A novel proximity assay for the detection of proteins and protein complexes: quantitation of HER1 and HER2 total protein expression and homodimerization in formalin-fixed, paraffin-embedded cell lines and breast cancer tissue," Diagn. Mol. Pathol. 18(1):11-21 (2009) (pub. Mar. 2009).

Chan-Hui, P-Y et al., "Applications of eTag™ assay platform to systems biology approaches in molecular oncology and toxicology studies," Clin. Immun. 111:162-174 (2004) (pub. online Mar. 11, 2004).

Tian, H. et al., "Multiplex mRNA assay using electrophoretic tags for high-throughput gene expression analysis," Nucl. Acid Res. 32(16):e126 (pub. online Sep. 8, 2004).

International Patent Application No. PCT/US2017/022566, International Preliminary Report on Patentability and Written Opinion dated Sep. 27, 2018.

Wallweber, G. et al., "Development of a proximity-based immunoassay to measure the PD1:PD-L1 complex in fixed samples," 107th Annual American Association for Cancer Research (AACR) Meeting, Apr. 16-20, 2016, New Orleans, LA (Poster 3225).

Dua et al., "Detection of Hepatocyte Growth Factor (HGF) Ligand-c-MET Receptor Activation in Formalin-Fixed Paraffin Embedded Specimens by a Novel Proximity Assay", PLos One, Vo. 6, No. 1, Jan. 1, 2011, 17 pages.

PCT/US2017/022566 , "International Search Report and Written Opinion", dated Jun. 20, 2017, 14 pages.

Pollock et al., "Increased Expression of HER2. HER3. And HER2:HER3 Heterodimers in HPV-Positive HNSCC Using a Novel Proximity-Based Assay: Implications for Targeted Therapies", Clinical Cancer Research, vol. 21. No. 20, Oct. 15, 2015, pp. 4597-4606.

Shi et al., "A Novel Proximity Assay for the Detection of Proteins and Protein Complexes: Quantitation of HER1 and HER2 Total Protein Expression and Homodimerization in Formalin-fixed. Paraffin-Embedded Cell Lines and Breast Cancer Tissue", Diagnostic Molecular Pathology, vol. 18. No. 1., Mar. 1, 2009, pp. 11-21.

Wallweber et al., "Abstract #3225: Development of a proximity-based immunoassay to measure the PD1:PD-L1 complex in fixed samples", aacr Annual Meeting 2016 Retrieved from the Internet at URL: http://www.abstractsonline.com/Plan/ViewAbstract.aspx?sKey=afd544f7-410d-4cd6-b69d-203febb0b09b&cKey=7d98dbab-87f7-4fa7-b6e0-b76603de2ed1&mKey={1D100749-4B6A-4AB3-BCD4-F80FB1922267}, Apr. 19, 2016.

Japanese Patent Application No. 2018-548307, Office Action dated Jan. 23, 2019 (7 pages).

* cited by examiner

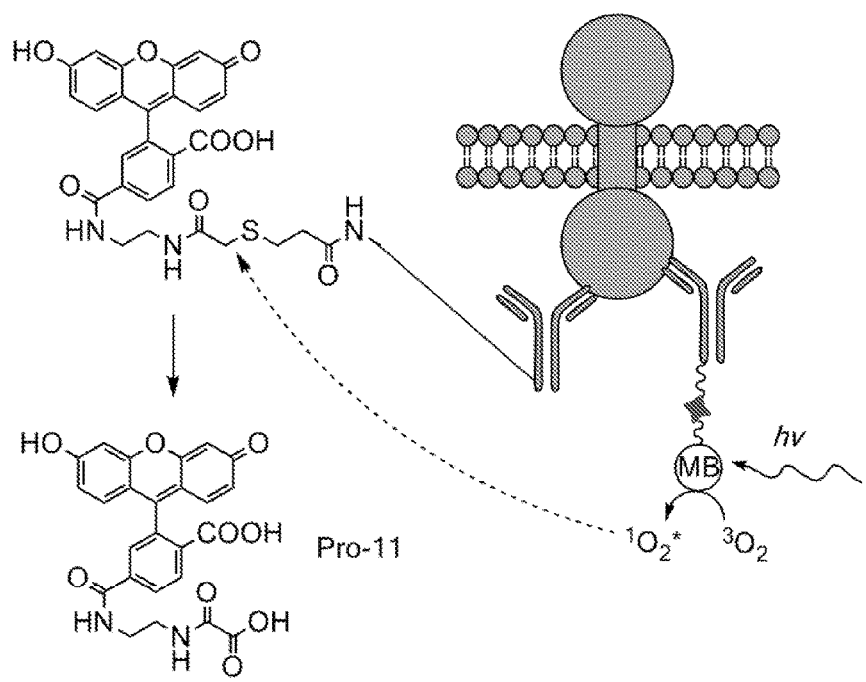
FIG. 1C
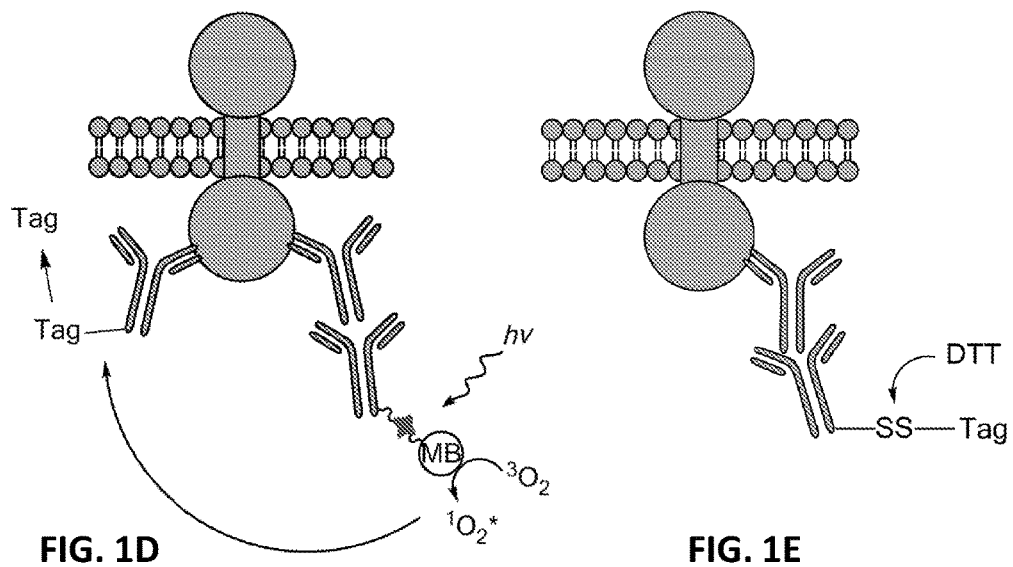
FIG. 1D
FIG. 1E

Complex vs PD1

Pearson $R^2$ = 0.7638
p value = 0.0002

Complex vs PD-L1

Pearson $R^2$ = 0.3657
p value = 0.1123

PD-L1 vs PD1

Pearson $R^2$ = 0.5612
p value = 0.0324

METHODS OF ASSESSING PROTEIN INTERACTIONS BETWEEN CELLS

CROSS-REFERENCE TO RELATED APPLICATIONS

This application is the national stage entry of the international application no. PCT/US2017/022566, filed Mar. 15, 2017, which claims the benefit of and priority under 35 U.S.C. § 119(e) to U.S. Provisional Application No. 62/308,587, filed Mar. 15, 2016. Each of the aforementioned applications are incorporated herein by reference in its entirety.

BACKGROUND

Proteins control all biological systems in a cell. While many proteins perform their functions independently, the vast majority of proteins interact with others for proper biological activity. The function and activity of a protein are often modulated by other proteins with which it interacts. As cells respond to myriad of stimuli, protein expression can be a transient or dynamic process. In addition, different types of cells, can express different types of proteins (cell type-dependent or -specific expression). Characterizing protein-protein interactions is important to understand protein function and the biology of the cell. While there are various methods that can be used to assess protein-protein interactions, the task can become more difficult when the proteins that interact are expressed on different cells. The methods described herein provide means for facilitating detection and quantitation of such protein-protein interactions between cells.

BRIEF SUMMARY

In one aspect, provided is a method of quantifying a protein-protein interaction in a sample, the method including the steps of: (a) providing a sample comprising a first cell expressing a first protein on its cell surface and a second cell expressing a second protein on its cell surface; (b) providing a first antibody binding composition specific for the first protein, wherein the first antibody binding composition has a molecular tag attached thereto via a cleavable linkage; (c) providing a second antibody binding composition specific for the second protein, wherein the second binding composition has a cleavage inducing moiety attached thereto; (d) contacting the sample with the first antibody binding composition and the second antibody binding composition; (e) inducing cleavage of the molecular tag from the first antibody binding composition when the first antibody binding composition is within an effective proximity range of the cleavage inducing moiety attached to the second antibody binding composition, thereby releasing the molecular tag; and (f) quantitating the amount of released molecular tag as a measure of the amount of protein-protein interaction between the first protein and the second protein.

In another aspect, provided is a method of quantifying a protein-protein interaction in a sample, the method including the steps of: (a) providing a sample comprising a first cell expressing a first protein on its cell surface and a second cell expressing a second protein on its cell surface; (b) providing a first antibody binding composition specific for the first protein, wherein the first antibody binding composition has a molecular tag attached thereto via a cleavable linkage; (c) providing a second antibody binding composition specific for the second protein; (d) providing a third antibody composition that binds to the second antibody composition, the third antibody composition having a cleavage inducing moiety attached thereto; (e) contacting the sample with the first antibody binding composition, the second antibody binding composition, and the third antibody binding composition; (f) inducing cleavage of the molecular tag from the first antibody binding composition when the first antibody binding composition is within an effective proximity range of the cleavage inducing moiety attached to the third antibody binding composition, thereby releasing the molecular tag; and (g) quantitating the amount of released molecular tag as a measure of the amount of protein-protein interaction between the first protein and the second protein.

In another aspect, provided is a method of quantifying a protein-protein interaction in a sample, the method including the steps of: (a) providing a sample comprising a first cell expressing a first protein on its cell surface and a second cell expressing a second protein on its cell surface; (b) providing a first antibody binding composition specific for the first protein, the first antibody composition having a cleavage inducing moiety attached thereto; (c) providing a second antibody binding composition specific for the second protein; (d) providing a third antibody composition that binds to the second antibody composition, the third antibody binding composition having a molecular tag attached thereto via a cleavable linkage; (e) contacting the sample with the first antibody binding composition, the second antibody binding composition, and the third antibody binding composition; (f) inducing cleavage of the molecular tag from the third antibody binding composition when the third antibody binding composition is within an effective proximity range of the cleavage inducing moiety attached to the first antibody binding composition, thereby releasing the molecular tag; and (g) quantitating the amount of released molecular tag as a measure of the amount of protein-protein interaction between the first protein and the second protein.

In yet another aspect, provided is a method of quantifying a protein-protein interaction in a sample, the method including the steps of: (a) providing a sample comprising a first cell expressing a first protein on its cell surface and a second cell expressing a second protein on its cell surface; (b) providing a first antibody binding composition specific for the first protein; (c) providing a second antibody binding composition specific for the second protein; (d) providing a third antibody composition that binds to the first antibody composition, the third antibody composition having a molecular tag attached thereto via a cleavable linkage; (e) providing a fourth antibody composition that binds to the second antibody composition, the fourth antibody composition having a cleavage inducing moiety attached thereto; (e) contacting the sample with the first antibody binding composition, the second antibody binding composition, the third antibody binding composition, and the fourth antibody binding composition; (f) inducing cleavage of the molecular tag from the third antibody binding composition when the third antibody binding composition is within an effective proximity range of the cleavage inducing moiety attached to the fourth antibody binding composition, thereby releasing the molecular tag; and (g) quantitating the amount of released molecular tag as a measure of the amount of protein-protein interaction between the first protein and the second protein.

In some instances, the first antibody binding composition may bind to an extracellular domain epitope or an intracellular domain epitope of the first protein. In other instances, the second antibody binding composition may bind to an extracellular domain epitope or an intracellular domain epitope of the second protein. In some instances, the cleavage of the molecular tag by the cleavage inducing moiety is induced by light.

In some instances, the sample may be a tissue sample, cultured cells, or peripheral blood mononuclear cells (PMBCs). The sample may be a cancer biopsy sample. The sample may be a formalin-fixed paraffin-embedded (FFPE) sample. The sample may be a blood sample.

In some instances, the first cell may be a T cell and the second cell may be a tumor cell. In some instances, the first protein is PD-1 and the second protein is PD-L1.

In another aspect, provided is a method for predicting responsiveness of a subject having a cancer to a PD-1 or PD-L1 acting agent, the method including the steps of: (a) measuring the amount of PD-1-PD-L1 complex in a biological sample from the subject's cancer using any of the methods described above; (b) determining whether the amount of PD-1-PD-L1 complex in the subject's sample is above or below a threshold level; and (c) indicating that the subject is more likely to respond to the PD-1 or PD-L1 acting agent if the amount of PD-1-PD-L1 complex in the subject's sample is equal to or above the threshold level than if the amount of PD-1-PD-L1 complex is below the threshold level.

In another aspect, provided is a method of screening test agents for the ability to disrupt or promote formation of a protein-protein interaction between two cells in a sample, the method having the steps of: (a) contacting a test cell culture with a test agent, the test cell culture comprising a first cell expressing a first protein on its cell surface and a second cell expressing a second protein on its cell surface; (b) measuring the amount of protein-protein interaction between the first protein and the second protein using any of the methods described above; and (c) comparing the amount of protein-protein interaction measured in step (b) to the amount of protein-protein interaction measured between the first protein and the second protein in a control cell culture not contacted with the test agent, the control cell culture comprising the first cell expressing the first protein on its cell surface and the second cell expressing the second protein on its cell surface.

In some instances, the test agent may be an inhibitor of the protein-protein interaction between the first protein and the second protein if the amount of protein-protein interaction is decreased in the test cell culture as compared to the control cell culture. In other instances, the test agent may be a promoter of the protein-protein interaction between the first protein and the second protein if the amount of protein-protein interaction is increased in the test cell culture as compared to the control cell culture.

In some instances, the first cell and the second cell may be different cell types. In some instances, the first cell and the second cell may be different cancer cell lines. In some instances, one of the first cell and the second cell in an adherent cell line and the other is a non-adherent cell line. In some instances, the first cell is a Jurkat cell and the second cell is an adherent cancer cell.

BRIEF DESCRIPTION OF THE DRAWINGS

FIGS. 1A-1E are diagrams showing schematic representations of various VeraTag® assay formats according to some aspects of the disclosure. FIG. 1A and FIG. 1B depict analysis of formalin-fixed paraffin-embedded (FFPE) tissue samples, with FIG. 1A showing a light release assay format and FIG. 1B showing a reducing (e.g., DTT) assay format. In the light release format, diffusing reactive singlet oxygen may be used to cleave the covalent linker between a VeraTag® reporter molecule ("Tag") and a target-specific antibody ("1° Ab") in response to photo-induction of the cleavage-inducing agent by light ("hv"). In the reducing format, a reducing agent is used to induce cleavage of the covalent linker between a VeraTag® reporter molecule ("Tag") and a secondary antibody ("2° Ab"). Following cleavage, capillary electrophoretic (CE) separation of the VeraTag® reporter molecules may be conducted and assessed by electropherogram. The x-axis shows the time at which the cleaved VeraTag® reporter molecule eluted from the capillary, and the fluorescence intensity is shown on the y-axis. Fluorescent peaks MF and ML denote the elution of two different, internal VeraTag® reporter molecules.

FIG. 1C shows a schematic representation of a light release assay format for detecting a single protein in which the reporter molecule (such as Pro11) and a cleavage inducing moiety are linked to separate target-specific antibodies binding distinct epitopes. The cleavage inducing moiety, also referred to "molecular scissors", is attached to a second primary antibody. An exemplary moiety is streptavidin (square-ish shape)-conjugated methylene blue (MB). FIG. 1D shows a schematic representation of another light release assay format for detecting a single protein using a first target-specific antibody linked to a reporter molecule, a second target-specific antibody that binds a distinct epitope from the first target-specific antibody, and a secondary antibody that binds to the second target-specific antibody and to which a cleavage inducing moiety is linked. FIG. 1E shows a schematic representation of a reducing assay format for detecting a single protein using a target-specific antibody and a secondary antibody that binds to the target-specific antibody and to which a reporter molecule is linked via a linker containing a disulfide bond that is cleavable by a reducing agent (e.g., DTT).

DETAILED DESCRIPTION

Figure 1A:
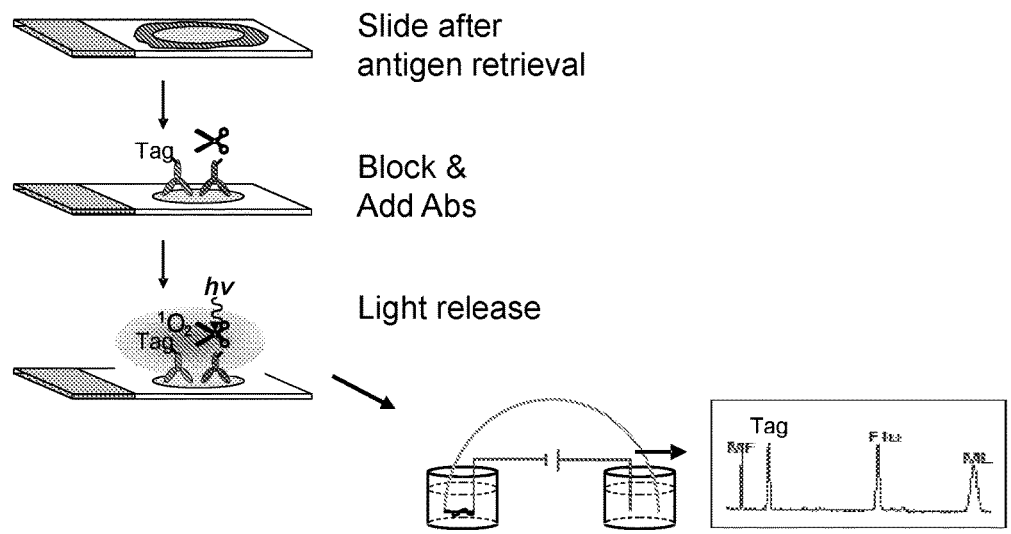

The features and attendant advantages of embodiments of the provided technology will become apparent and further understood by reference to the following detailed description when considered in conjunction with the accompanying drawings.

Provided are methods of detecting and quantitating an amount of protein-protein interaction between proteins expressed on different cells. In particular, the described methods are useful for detecting and quantitating extracellular receptor-ligand interactions. Also provided are methods of using such measurements clinically for any of classifying patient disease status (such as cancer status), indicating patient prognosis, or indicating patient responsiveness to treatment.

In one aspect, provided is a method of quantifying a protein-protein interaction in a sample, the method comprising: (a) providing a sample comprising a first cell expressing a first protein on its cell surface and a second cell expressing a second protein on its cell surface; (b) providing a first antibody binding composition specific for the first protein, wherein the first antibody binding composition comprises a molecular tag attached thereto via a cleavable linkage; (c) providing a second antibody binding composition specific for the second protein, wherein the second binding composition comprises a cleavage inducing moiety attached thereto; (d) contacting the sample with the first antibody binding composition and the second antibody binding composition; (e) inducing cleavage of the molecular tag from the first antibody binding composition when the first antibody binding composition is within an effective proximity range of the cleavage inducing moiety attached to the second antibody binding composition, thereby releasing the molecular tag; and (f) quantitating the amount of released molecular tag as a measure of the amount of protein-protein interaction between the first protein and the second protein. Examples of this type of assay are shown schematically in FIG. 1A, FIG. 1F, and FIG. 1G. The sample may be a tissue sample, cultured cells, or peripheral blood mononuclear cells (PMBCs). The first antibody binding composition may bind to an extracellular domain epitope or an intracellular domain epitope of the first protein. The second antibody binding composition may bind to an extracellular domain epitope or an intracellular domain epitope of the second protein.

In another aspect, provided is a method of quantifying a protein-protein interaction in a sample, the method comprising: (a) providing a sample comprising a first cell expressing a first protein on its cell surface and a second cell expressing a second protein on its cell surface; (b) providing a first antibody binding composition specific for the first protein, wherein the first antibody binding composition comprises a molecular tag attached thereto via a cleavable linkage; (c) providing a second antibody binding composition specific for the second protein; (d) providing a third antibody composition that binds to the second antibody composition, the third antibody composition comprising a cleavage inducing moiety attached thereto; (e) contacting the sample with the first antibody binding composition, the second antibody binding composition, and the third antibody binding composition; (f) inducing cleavage of the molecular tag from the first antibody binding composition when the first antibody binding composition is within an effective proximity range of the cleavage inducing moiety attached to the third antibody binding composition, thereby releasing the molecular tag; and (g) quantitating the amount of released molecular tag as a measure of the amount of protein-protein interaction between the first protein and the second protein. An example of this type of assay is shown schematically in FIG. 1H. The sample may be a tissue sample, cultured cells, or peripheral blood mononuclear cells (PMBCs). The first antibody binding composition may bind to an extracellular domain epitope or an intracellular domain epitope of the first protein. The second antibody binding composition may bind to an extracellular domain epitope or an intracellular domain epitope of the second protein.

In another aspect, provided is a method of quantifying a protein-protein interaction in a sample, the method comprising: (a) providing a sample comprising a first cell expressing a first protein on its cell surface and a second cell expressing a second protein on its cell surface; (b) providing a first antibody binding composition specific for the first protein, the first antibody composition comprising a cleavage inducing moiety attached thereto; (c) providing a second antibody binding composition specific for the second protein; (d) providing a third antibody composition that binds to the second antibody composition, the third antibody binding composition comprising a molecular tag attached thereto via a cleavable linkage; (e) contacting the sample with the first antibody binding composition, the second antibody binding composition, and the third antibody binding composition; (f) inducing cleavage of the molecular tag from the third antibody binding composition when the third antibody binding composition is within an effective proximity range of the cleavage inducing moiety attached to the first antibody binding composition, thereby releasing the molecular tag; and (g) quantitating the amount of released molecular tag as a measure of the amount of protein-protein interaction between the first protein and the second protein. A schematic for this type of assay is not shown but is readily envisioned from that shown in FIG. 1H. The sample may be a tissue sample, cultured cells, or peripheral blood mononuclear cells (PMBCs). The first antibody binding composition may bind to an extracellular domain epitope or an intracellular domain epitope of the first protein. The second antibody binding composition may bind to an extracellular domain epitope or an intracellular domain epitope of the second protein.

In yet another aspect, provided is a method of quantifying a protein-protein interaction in a sample, the method comprising: (a) providing a sample comprising a first cell expressing a first protein on its cell surface and a second cell expressing a second protein on its cell surface; (b) providing a first antibody binding composition specific for the first protein; (c) providing a second antibody binding composition specific for the second protein; (d) providing a third antibody composition that binds to the first antibody composition, the third antibody composition comprising a molecular tag attached thereto via a cleavable linkage; (e) providing a fourth antibody composition that binds to the second antibody composition, the fourth antibody composition comprising a cleavage inducing moiety attached thereto; (e) contacting the sample with the first antibody binding composition, the second antibody binding composition, the third antibody binding composition, and the fourth antibody binding composition; (f) inducing cleavage of the molecular tag from the third antibody binding composition when the third antibody binding composition is within an effective proximity range of the cleavage inducing moiety attached to the fourth antibody binding composition, thereby releasing the molecular tag; and (g) quantitating the amount of released molecular tag as a measure of the amount of protein-protein interaction between the first protein and the second protein. An example of this type of assay is shown schematically in FIG. 1I. The sample may be a tissue sample, cultured cells, or peripheral blood mononuclear cells (PMBCs). The first antibody binding composition may bind to an extracellular domain epitope or an intracellular domain epitope of the first protein. The second antibody binding composition may bind to an extracellular domain epitope or an intracellular domain epitope of the second protein.

In one aspect, the methods provided are useful for detecting the interaction between proteins expressed on the surface of immune cells (such as T cells) and proteins expressed on the surface of cancer cells. There are various ligand-receptor interactions between T cells and antigen-presenting cells (APCs) that regulate the T cell response to antigen. Immune checkpoint molecules can be stimulatory (turn up a signal) or inhibitory (turn down signal). Inhibitory checkpoint molecules on immune cells, when engaged by their ligands, transmit an inhibitory signal, maintain self-tolerance, and regulate the duration and amplitude of immune responses in peripheral tissues to minimize tissue pathology. Cancer cells can use these pathways to protect themselves from the immune system by inhibiting the T cell signal. Exemplary immune checkpoint molecules are listed in Table 1. In general, the checkpoint molecule is expressed on a T cell, while the ligand is expressed on an antigen-presenting cell, such as a cancer cell. An exception to this is that CD40 is expressed on cancer cells, while CD40L is expressed on T cells (exception marked with * in Table 1 below). There may be other exceptions as well. The detection of such protein-protein interactions in a sample, particularly a tumor sample, may reflect the degree to which immune cells are present in a sample. When the sample is a tumor sample, the amount of protein-protein interaction represents the amount of activated immune checkpoint complex in the sample.

TABLE 1

Immune checkpoint molecules

| | Ligands |
|---|---|
| Inhibitory molecules | |
| PD-1 | PD-L1 or PD-L2 |
| CTLA4 | CD80 or CD86 |
| BTLA4 | HVEM |
| TIM3 | GAL9 |
| Stimulatory molecules | |
| CD27 | CD70 |
| CD28 | CD80 or CD86 |
| CD40* | CD40L |
| CD137 | CD137L |
| OX40 | OX40L |
| ICOS | B7RP1 |
| GITR | GITRL |

In some instances, the first protein may be a receptor and the second protein may be a ligand for the receptor. In some instances, the first cell may be a T cell and the second cell may be an antigen-presenting cell. In one example, the antigen-presenting cell may be a tumor cell. In another example, the first protein may be PD-1 (also referred to as PD1 herein) and the second protein may be PD-L1 (also referred to as PDL1 herein). In another example, the first protein may be CD28 or CTLA4 and the second protein may be CD80 or CD86. In another example, the first protein may be BTLA4 and the second protein may be HVEM. In another example, the first protein may be TIM3 and the second protein may be GAL9. In another example, the first protein may be CD27 and the second protein may be CD70. In another example, the first protein may be CD40L and the second protein may be CD40. In another example, the first protein may be CD137 and the second protein may be CD137L. In another example, the first protein may be OX40 and the second protein may be OX40L. In another example, the first protein may be ICOS and the second protein may be B7RP1. In another example, the first protein may be GITR and the second protein may be CITRL. In some instances, the first cell may be a T cell and the first protein may be PD-1, CTLA4, BTLA4, TIM3, CD27, CD28, CD40L, CD137, OX40, ICOS, or GITR. In some instances, the second cell may be a tumor cell and the second protein may be PD-L1, PD-L2, CD80, CD86, HVEM, GAL9, CD70, CD40, CD137L, OX40L, B7RP1, or GITRL.

In some instances, the amount of the first protein, the second protein, or both, may be determined in addition to quantitation of the amount of complex between the two proteins. For example, this may be a threshold measurement taken to determine if the first protein and/or the second protein are present in the sample. In some instances, this step may be performed to determine whether one of the proteins is more limited than the other and, in some instances, to what extent. In some instances, where the sample is a tumor sample and the first cell is a T cell, the method involves quantitating the amount of the first protein to determine the amount of T cell infiltration in the tumor. If there is a large amount of the first protein present, it may indicate that there are large numbers of activated T cells infiltrating the tumor. If there is a small amount of the first protein present, it may indicate that there are few activated T cells present in the tumor. In some instances, the responsiveness of a patient to a therapy directed to the first protein or the second protein (for example, in terms of how quickly the patient responds to such therapy) may be increased where there is a large number of activated T cells present in the tumor.

Features of VeraTag® Assays

Figure 1B:
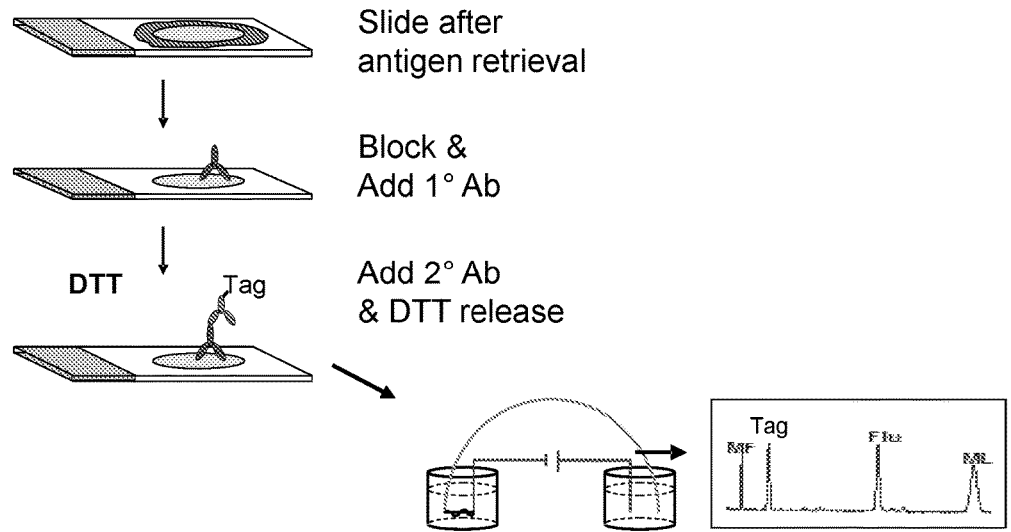

In certain embodiments, the amount of protein complex in a sample are determined by contacting a sample with an antibody binding composition having a molecular tag attached thereto via a cleavable linkage and an antibody binding composition having a cleavage inducing-moiety attached thereto, and detecting the amount of molecular tag is released. FIGS. 1A, 1C, 1F, 1G, 1H, and 1I provide schematic diagrams of exemplary VeraTag® assay formats. In one example, as shown in FIG. 1A, a sample (tissue section, cultured cells) is fixed and then allowed to bind with a first antibody binding composition having a cleavage-inducing agent and a second antibody binding composition linked to a detectable moiety such as a molecular tag (for example, a VeraTag® reporter molecule). The first antibody may be conjugated to biotin, which is then bound with a cleavage inducing moiety, for example, a streptavidin-functionalized sensitizer dye (methylene blue). The second antibody binding composition is conjugated to a VeraTag® reporter molecule or other suitable detectable moiety. Photoinduction of the cleavage-inducing agent may be performed to cause the release of singlet oxygen, which induces cleavage of the cleavable linkage and release of the VeraTag® reporter molecule into the assay solution. The solution is then collected and analyzed by capillary electrophoresis. Exemplary schematics of this assay format are shown in FIGS. 1C, 1F, 1G, 1H, and 1I. FIGS. 1D, 1G, and 1I have different antibody binding composition pairings but are shown with the same exemplary VeraTag® assay chemistry as described for FIG. 1A.

Figure 1F:
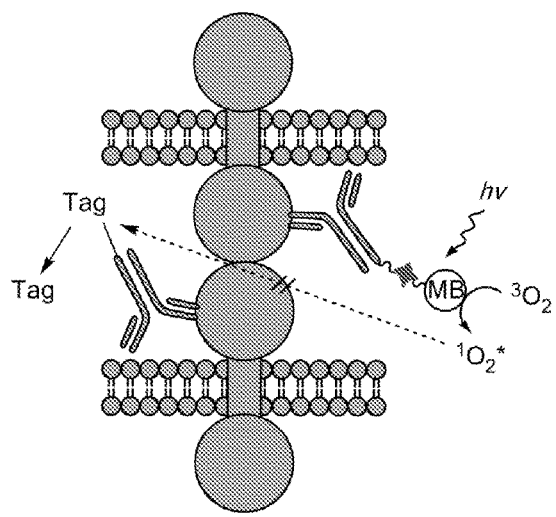
FIG. 1F and FIG. 1G shows a schematic representation of a light release assay format for detecting a protein-protein interaction between a first protein expressed on the surface of a first cell and a second protein expressed on the surface of a second cell, with FIG. 1F showing the use of two target-specific antibodies that bind to the extracellular domains of the first and second proteins, respectively, and FIG. 1G showing the use of a first target-specific antibody that binds to the extracellular domain of the first protein and a second target-specific antibody that bind to the intracellular domain of the second protein. A reporter molecule and a cleavage inducing moiety are linked to one of the target-specific antibodies, respectively.
Figure 1G:
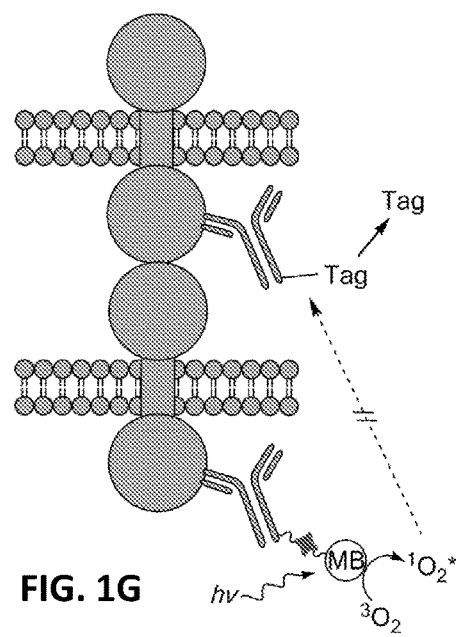

In some instances, the first antibody binding composition may specifically bind to a first protein and the second antibody binding composition may bind specifically to a second protein as shown, for example, in FIG. 1F and FIG. 1G. This assay format permits detection of complexes formed between the first protein and the second protein as the molecular tag may be cleaved when the molecular tag attached to the first antibody binding composition is within an effective proximity of the cleavage-inducing moiety attached to the second antibody binding composition. In some instances, the molecular tag may be attached to a third antibody composition that binds to the first antibody composition instead of being attached to the first antibody as shown, for example, in FIG. 1H. In other instances, the cleavage inducing moiety may be attached to a third antibody composition that binds to the second antibody composition instead of being attached to the second antibody. In other instances, the molecular tag may be attached to a third antibody composition that binds to the first antibody composition instead of being attached to the first antibody and the molecular tag may be attached to a fourth antibody composition that binds to the second antibody composition instead of being attached to the second antibody as shown, for example, in FIG. 1I.

In certain instances, a VeraTag® assay may be used to detect a total amount of a protein in a sample. In such assays, a first antibody binding composition and second antibody binding composition may both specifically bind to the same protein target but to distinct epitopes. In certain embodiments, a first antibody binding composition with a molecular tag attached thereto and a second antibody binding composition with a cleavage inducing moiety attached thereto bind the same target protein but do not bind the same epitope of the target protein. Such an assay format is shown, for example, in FIG. 1C. In another format, a first antibody binding composition with a molecular tag attached thereto binds to a first epitope, a second antibody binding composition binds to a second epitope different than the first epitope, and a third antibody composition with a cleavage inducing moiety attached thereto binds to the second antibody binding composition. Such an assay format is shown, for example, in FIG. 1D. In another format, the first antibody binding composition binds to a first epitope, a second antibody binding composition with a molecular tag attached thereto binds to the first antibody binding composition, and a third antibody composition with a cleavage inducing moiety attached thereto binds to a second epitope different than the first epitope. In each of these formats, when the molecular tag is within an effective proximity of the cleavage-inducing moiety, the cleavage-inducing moiety may cleave the cleavable linker so that the molecular tag is released. In some instances, this type of assay format measures the total amount of a target protein in a sample. Examples of detection of total HER2 using a similar assay format is described in commonly owned U.S. Patent Application Publication No. 2009/0191559 incorporated by reference in its entirety herein. A similar assay format as described with respect to measuring total amounts of biomarkers such as HER1, HER3, cMET, and the like, as described in U.S. Pat. Nos. 7,648,828 and 8,349,574 may also be used.

In an alternative embodiment, a total amount of protein may be detected using a reducing format assay as shown in FIG. 1E, wherein a first antibody binding composition binds specifically to the target protein and a second antibody composition binds to the first antibody binding composition, the second antibody binding composition comprising the detectable moiety conjugated thereto via a cleavable linkage such as a disulfide bond (—SS—), which is cleavable via a reducing agent such as DTT.

"Antibody binding composition" is used herein to refer to a molecule or a complex of molecules that comprises one or more antibodies, or antigen-binding fragments that bind to a molecule, and derives its binding specificity from such antibody or antibody-binding fragment. Antibody binding compositions include, but are not limited to, (i) antibody pairs in which a first antibody binds specifically to a target molecule and a second antibody binds specifically to a constant region of the first antibody; a biotinylated antibody that binds specifically to a target molecule and a streptavidin protein, which protein is derivatized with moieties such as molecular tags or photosensitizers or the like, via a biotin moiety; (ii) antibodies specific for a target molecule and conjugated to a polymer, such as dextran, which, in turn, is derivatized with moieties such as molecular tags or photosensitizers, either directly by covalent bonds or indirectly via streptavidin-biotin linkages; (iii) antibodies specific for a target molecule and conjugated to a bead, or microbead, or other solid phase support, which, in turn, is derivatized either directly or indirectly with moieties such as molecular tags or photosensitizers, or polymers containing the latter.

"Cleavage-inducing moiety" and "cleaving agent" are used interchangeably herein to refer to a group that produces an active species that is capable of cleaving a cleavable linkage, for example, by oxidation. Preferably, the active species is a chemical species that exhibits short-lived activity so that its cleavage-inducing effects are only in the proximity of the site of its generation.

A "molecular tag" or "tag" or "reporter molecule" or "detectable moiety" as used herein refers to a molecule that can be distinguished from other molecules based on one or more physical, chemical or optical differences among the molecules being separated, including but not limited to, electrophoretic mobility, molecular weight, shape, solubility, pKa, hydrophobicity, charge, charge/mass ratio, polarity or the like. In one aspect, molecular tags in a plurality or set differ in electrophoretic mobility and optical detection characteristics and can be separated by electrophoresis. In another aspect, molecular tags in a plurality or set may differ in molecular weight, shape, solubility, pKa, hydrophobicity, charge, polarity and can be separated by normal phase or reverse phase HPLC, ion exchange HPLC, capillary electrochromatography, mass spectroscopy, gas phase chromatography or like technique. As described herein, a VeraTag® reporter molecule is a type of molecular tag.

"Photosensitizer" shall mean a light-adsorbing molecule that when activated by light converts molecular oxygen into singlet oxygen. As used herein, "dithiothreitol" or "DTT" may be used as a substitute for a photosensitizer to cleave the VeraTag® reporter molecule by reduction.

The terms "sample," "tissue sample," "patient sample," "patient cell or tissue sample," or "specimen" each refer to a collection of similar cells obtained from a tissue of a subject or patient. The source of the tissue sample may be solid tissue as from a fresh, frozen, and/or preserved organ or tissue sample or biopsy or aspirate; blood or any blood constituents; bodily fluids such as cerebral spinal fluid, amniotic fluid, peritoneal fluid or interstitial fluid; or cells from any time in gestation or development of the subject. The tissue sample may contain compounds that are not naturally intermixed with the tissue in nature such as preservatives, anticoagulants, buffers, fixatives, nutrients, antibiotics or the like. Cells may be fixed in a conventional manner (e.g., formalin-fixed, paraffin-embedding (FFPE)).

"VeraTag®" and "VeraTag® assay" are used interchangeably herein and refer to single and multiplexed immunoassays, both single- and multi-label format, and the materials, methods and techniques for performing and utilizing such assays, including but not limited to reagents, analytical procedures and software related to those assays. Labels in the context of a VeraTag® assay are detectable moieties that are referred to as VeraTag® reporter molecules. Such assays are disclosed in this application as well as in U.S. Pat. Nos. 7,648,828; 8,470,542; and 8,349,574; and U.S. Patent Application Nos. 2012-0295259 and 2016-0041171, all of which are incorporated by reference herein in their entireties.

Figure 1H:
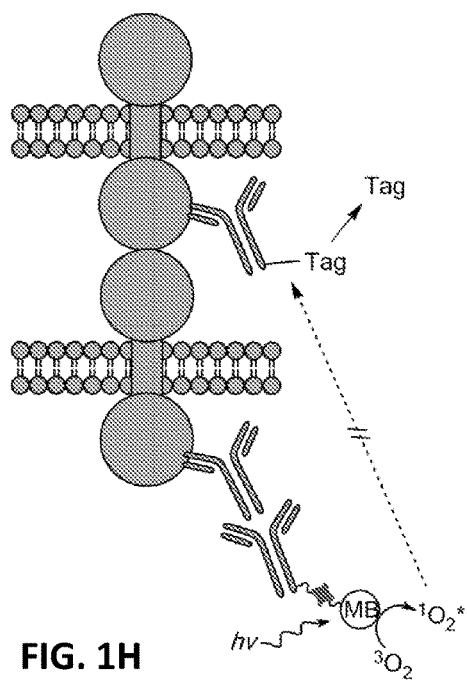
FIG. 1H shows a schematic representation of another light release assay format for detecting a protein-protein interaction between a first protein expressed on the surface of a first cell and a second protein expressed on the surface of a second cell, the assay format using a first target-specific antibody binds to the first protein and has a reporter molecule linked to it, a second target-specific antibody binds to the second protein, and a secondary antibody that binds to the second target-specific antibody and has a cleavage inducing moiety linked thereto.
Figure 1I:
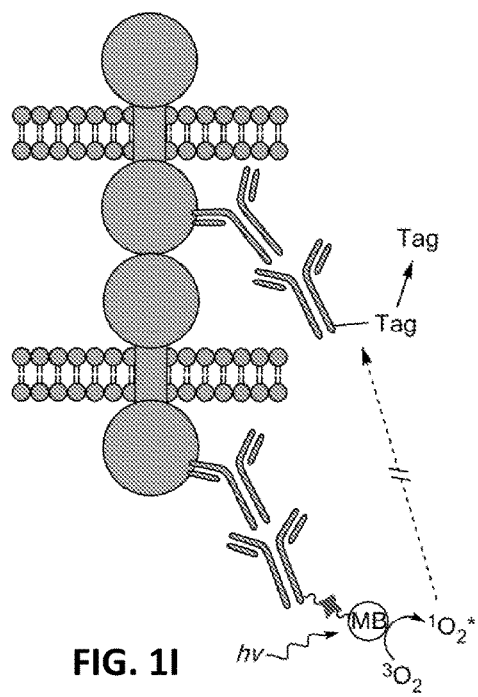
FIG. 1I shows a schematic representation of another light release assay format for detecting a protein-protein interaction between a first protein expressed on the surface of a first cell and a second protein expressed on the surface of a second cell, the assay format using a first target-specific antibody that binds the first protein, a first secondary antibody that binds to the first target-specific antibody and is linked to a reporter molecule, a second target-specific antibody, and a second secondary antibody that binds to the second target-specific antibody and is linked to a cleavage inducing moiety.
Figure 1J:
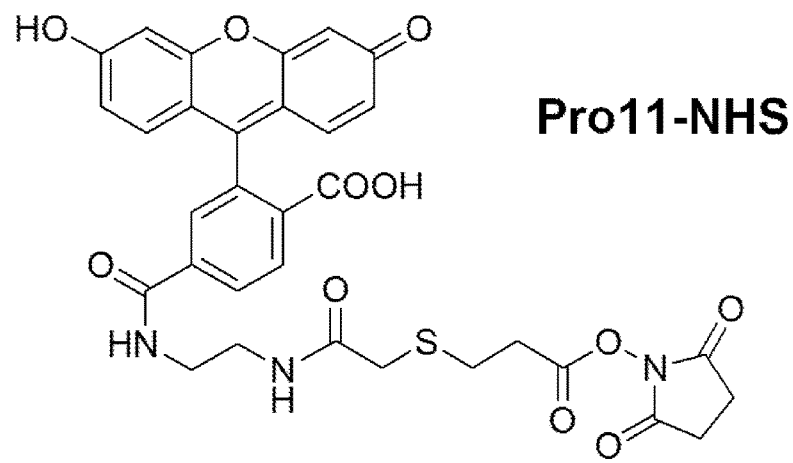
FIG. 1J shows the chemical structure of VeraTag® reporter molecules Pro11-NHS and Pro125-NHS prior to conjugation to an antibody (the NHS moiety is lost upon conjugation) according to some aspects of the disclosure.
Figure 1J:
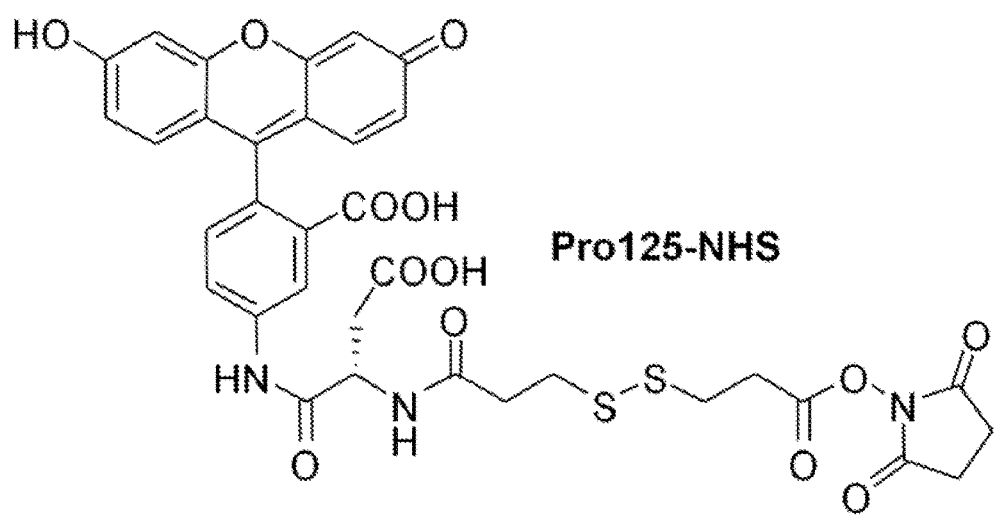

As used herein, "VeraTag® reporter molecule" or "vTag" refer to a type of molecular tag (as defined above) that is attached to an antibody used in a VeraTag® assay. Exemplary VeraTag® reporter molecules are Pro11 and Pro125, which are shown in FIG. 1J. Other VeraTag® molecules are described in U.S. Pat. Nos. 6,627,400; 7,105,308; 7,255,999; 9,110, 975; 7,402,397; and 8,357,277, each of which are incorporated in their entireties herein for all purposes.

Many advantages are provided by measuring protein-protein interactions using releasable molecular tags, including (1) separation of released molecular tags from an assay mixture provides greatly reduced background and a significant gain in sensitivity; and (2) the use of molecular tags that are specially designed for ease of separation and detection provides a convenient multiplexing capability so that multiple receptor complex components may be readily measured simultaneously in the same assay. Assays employing such tags can have a variety of forms and are disclosed in the following references: U.S. Pat. Nos. 7,105,308 and 6,627,400; published U.S. Patent Application Nos. 2002/0013126, 2003/0170915, 2002/0146726, 2009/0191559, 2010/0143927, 2010/0233732, and 2010/0210034, each of which are incorporated herein by reference in their entireties. For example, a wide variety of separation techniques may be employed that can distinguish molecules based on one or more physical, chemical or optical differences among molecules being separated including electrophoretic mobility, molecular weight, shape, solubility, pKa, hydrophobicity, charge, charge/mass ratio or polarity. In one aspect, molecular tags in a plurality or set differ in electrophoretic mobility and optical detection characteristics and are separated by electrophoresis. In another aspect, molecular tags in a plurality or set may differ in molecular weight, shape, solubility, pKa, hydrophobicity, charge, polarity and are separated by normal phase or reverse phase HPLC, ion exchange HPLC, capillary electrochromatography, mass spectroscopy or gas phase chromatography.

Sets of molecular tags are provided that can be separated into distinct bands or peaks by a separation technique after they are released from binding compounds. Identification and quantification of such peaks provides a measure or profile of the presence and/or amounts of proteins, protein complexes and post-translationally modified proteins. Molecular tags within a set may be chemically diverse; however, for convenience, sets of molecular tags are usually chemically related. For example, they may all be peptides or they may consist of different combinations of the same basic building blocks or monomers or they may be synthesized using the same basic scaffold with different substituent groups for imparting different separation characteristics. The number of molecular tags in a plurality may vary depending on several factors including the mode of separation employed, the labels used on the molecular tags for detection, the sensitivity of the binding moieties and the efficiency with which the cleavable linkages are cleaved.

Measurements made directly on tissue samples may be normalized by including measurements on cellular or tissue targets that are representative of the total cell number in the sample and/or the numbers of particular subtypes of cells in the sample. The additional measurement may be preferred, or even necessary, because of the cellular and tissue heterogeneity in patient samples, particularly tumor samples, which may comprise substantial fractions of normal cells.

In some instances, tissue samples include, but are not limited to, breast, prostate, ovary, colon, lung, endometrium, stomach, salivary gland, larynx, pharynx, tongue, or pancreas tissue samples. Tissue samples can be obtained by a variety of procedures including surgical excision, aspiration or biopsy. The tissue may be fresh or frozen. In one embodiment, assays of the invention are carried out on tissue samples that have been fixed and embedded in paraffin and a step of deparaffination is be carried out. A tissue sample may be fixed (i.e., preserved) by conventional methodology. See, e.g., Lee G. Luna, HT (ASCP) Ed., 1960, *Manual of Histological Staining Method of the Armed Forces Institute of Pathology* 3$^{rd}$ edition, The Blakston Division McGraw-Hill Book Company, New York; Ulreka V. Mikel, Ed., 1994, *The Armed Forces Institute of Pathology Advanced Laboratory Methods in Histology and Pathology*, Armed Forces Institute of Pathology, American Registry of Pathology, Washington, D.C. One of skill in the art will appreciate that the choice of a fixative is determined by the purpose for which the tissue is to be histologically stained or otherwise analyzed. One of skill in the art will also appreciate that the length of fixation depends upon the size of the tissue sample and the fixative used.

Generally, a tissue sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology according to conventional techniques described by the references provided above. Examples of paraffin that may be used include, but are not limited to, Paraplast, Broloid, and Tissuemay. Once the tissue sample is embedded, the sample may be sectioned by a microtome according to conventional techniques. Sections may have a thickness in a range of about three microns to about twelve microns, and preferably, a thickness in a range of about 5 microns to about 10 microns. In one aspect, a section may have an area of about 10 $mm^2$ to about 1 $cm^2$. Once cut, the sections may be attached to slides by several standard methods. Examples of slide adhesives include, but are not limited to, silane, gelatin and poly-L-lysine. Paraffin embedded sections may be attached to positively charged slides and/or slides coated with poly-L-lysine.

If paraffin has been used as the embedding material, the tissue sections are generally deparaffinized and rehydrated to water prior to detection of biomarkers. Tissue sections may be deparaffinized by several conventional standard methodologies. For example, xylenes and a gradually descending series of alcohols may be used according to conventional techniques described by the references provided above. Alternatively, commercially available deparaffinizing non-organic agents such as Hemo-De® (CMS, Houston, Tex.) may be used.

As mentioned above, mixtures containing pluralities of different binding compounds may be provided, wherein each different binding compound has one or more molecular tags attached through cleavable linkages. The nature of the binding compound, cleavable linkage and molecular tag may vary widely. In one aspect, the antibody binding composition can be represented by the following formula:

wherein B is binding moiety (antibody); L is a cleavable linkage, and E is a molecular tag. In homogeneous assays, cleavable linkage, L, may be an oxidation-labile linkage, and more preferably, it is a linkage that may be cleaved by singlet oxygen as shown, for example, in FIG. 1A. Alternatively, it may be a linkage that is sensitive to cleavage by reduction, for example by DTT, as shown, for example, in FIG. 1B. The moiety "-(L-E)k" indicates that a single binding compound may have multiple molecular tags attached via cleavable linkages. In one aspect, k is an integer greater than or equal to one, but in other embodiments, k may be greater than several hundred, e.g., 100 to 500 or k is greater than several hundred to as many as several thousand, e.g., 500 to 5000. Usually each of the plurality of different types of binding compounds has a different molecular tag, E. Cleavable linkages, such as oxidation-labile linkages, and molecular tags, E, are attached to B by way of conventional chemistries.

Preferably, B is an antibody binding composition that specifically binds to a target. Antibody compositions are readily formed from a wide variety of commercially available antibodies, either monoclonal or polyclonal. In certain embodiments, B has a cleavable linkage, L, cleaved by a cleavage agent generated by the cleaving probe that acts over a short distance so that only cleavable linkages in the immediate proximity of the cleaving probe are cleaved.

Cleavable linkage, L, can be virtually any chemical linking group that may be cleaved under conditions that do not degrade the structure or affect detection characteristics of the released molecular tag, E. Typically, such an agent must be activated by making a physical or chemical change to the reaction mixture so that the agent produces a short lived active species that diffuses to a cleavable linkage to effect cleavage. In a homogeneous format, the cleavage agent is preferably attached to a binding moiety, such as an antibody, that targets prior to activation the cleavage agent to a particular site in the proximity of a binding compound with releasable molecular tags. In such embodiments, a cleavage agent is referred to herein as a "cleavage-inducing moiety."

Cleavable linkages may not only include linkages that are labile to reaction with a locally acting reactive species, such as hydrogen peroxide, singlet oxygen or the like, but also linkages that are labile to agents that operate throughout a reaction mixture, such as base-labile linkages, photocleavable linkages, linkages cleavable by reduction, linkages cleaved by oxidation, acid-labile linkages and peptide linkages cleavable by specific proteases. References describing many such linkages include Greene and Wuts, 1991, *Protective Groups in Organic Synthesis, Second Edition*, John Wiley & Sons, New York; Hermanson, 1996, *Bioconjugate Techniques*, Academic Press, New York; and U.S. Pat. No. 5,565,324.

In one aspect, commercially available cleavable reagent systems may be employed with the invention. For example, a disulfide linkage may be introduced between an antibody binding composition and a molecular tag using a heterofunctional agent such as N-succinimidyl 3-(2-pyridyldithio) propionate (SPDP), succinimidyloxycarbonyl-α-methyl-α-(2-pyridyldithio) toluene (SMPT) or the like, available from vendors such as Pierce Chemical Company (Rockford, Ill.). Disulfide bonds introduced by such linkages can be broken by treatment with a reducing agent, such as dithiothreitol (DTT), dithioerythritol (DTE), 2-mercaptoethanol or sodium borohydride. Typical concentrations of reducing agents to effect cleavage of disulfide bonds are in the range of about 1 mM to 100 mM. An oxidatively labile linkage may be introduced between an antibody binding composition and a molecular tag using the homobifunctional NHS ester cross-linking reagent, disuccinimidyl tartarate (DST) (available from Pierce) that contains central cis-diols that are susceptible to cleavage with sodium periodate (e.g., 15 mM periodate at physiological pH for 4 hours). Linkages that contain esterified spacer components may be cleaved with strong nucleophilic agents, such as hydroxylamine, e.g., 0.1 N hydroxylamine, pH 8.5, for 3-6 hours at 37° C. Such spacers can be introduced by a homobifunctional cross-linking agent such as ethylene glycol bis(succinimidylsuccinate)(EGS) available from Pierce (Rockford, Ill.). A base labile linkage can be introduced with a sulfone group. Homobifunctional cross-linking agents that can be used to introduce sulfone groups in a cleavable linkage include bis[2-(succinimidyloxycarbonyloxy)ethyl]sulfone (BSOCOES), and 4,4-difluoro-3,3-dinitrophenyl-sulfone (DFDNPS). Exemplary basic conditions for cleavage include 0.1 M sodium phosphate, adjusted to pH 11.6 by addition of Tris base, containing 6 M urea, 0.1% SDS, and 2 mM DTT, with incubation at 37° C. for 2 hours. Photocleavable linkages also include those disclosed in U.S. Pat. No. 5,986,076.

When L is oxidation labile, L may be a thioether or its selenium analog; or an olefin, which contains carbon-carbon double bonds, wherein cleavage of a double bond to an oxo group, releases the molecular tag, E. Illustrative oxidation labile linkages are disclosed in U.S. Pat. Nos. 6,627,400 and 5,622,929 and in published U.S. Patent Application Nos. 2002/0013126 and 2003/0170915; each of which is hereby incorporated herein by reference in its entirety.

Molecular tag, E, in the present invention may comprise an electrophoric tag as described in the following references when separation of pluralities of molecular tags are carried out by gas chromatography or mass spectrometry: See, e.g., Zhang et al., 2002, *Bioconjugate Chem.* 13:1002-1012; Giese, 1983, *Anal. Chem.* 2:165-168; and U.S. Pat. Nos. 4,650,750; 5,360,819; 5,516,931; and 5,602,273, each of which is hereby incorporated by reference in its entirety.

Molecular tag, E, is preferably a water-soluble organic compound that is stable with respect to the active species, especially singlet oxygen, and that includes a detection or reporter group. Otherwise, E may vary widely in size and structure. In one aspect, E has a molecular weight in the range of about 50 to about 2500 daltons, more preferably, from about 50 to about 1500 daltons. E may comprise a detection group for generating an electrochemical, fluorescent or chromogenic signal. In embodiments employing detection by mass, E may not have a separate moiety for detection purposes. Preferably, the detection group generates a fluorescent signal. Exemplary molecular tags Pro11 and Pro125 are shown in FIG. 1C and FIG. 1J.

In one aspect, molecular tag, E, is (M, D), where M is a mobility-modifying moiety and D is a detection moiety. The notation "(M, D)" is used to indicate that the ordering of the M and D moieties may be such that either moiety can be adjacent to the cleavable linkage, L. That is, "B-L-(M, D)" designates binding compound of either of two forms: "B-L-M-D" or "B-L-D-M."

Detection moiety, D, may be a fluorescent label or dye, a chromogenic label or dye or an electrochemical label. Preferably, D is a fluorescent dye. Exemplary fluorescent dyes for use with the invention include water-soluble rhodamine dyes, fluoresceins, 4,7-dichlorofluoresceins, benzoxanthene dyes and energy transfer dyes, as disclosed in the following references: *Handbook of Molecular Probes and Research Reagents*, 8$^{th}$ ed. (2002), Molecular Probes, Eugene, Oreg.; U.S. Pat. Nos. 6,191,278, 6,372,907, 6,096,723, 5,945,526, 4,997,928, and 4,318,846; and Lee et al., 1997, *Nucleic Acids Research* 25:2816-2822. Preferably, D is a fluorescein or a fluorescein derivative.

A cleavage-inducing moiety, or cleaving agent, is a group that produces an active species that is capable of cleaving a cleavable linkage, preferably by oxidation. Preferably, the active species is a chemical species that exhibits short-lived activity so that its cleavage-inducing effects are only in the proximity of the site of its generation. Either the active species is inherently short lived, so that it will not create significant background beyond the proximity of its creation, or a scavenger is employed that efficiently scavenges the active species, so that it is not available to react with cleavable linkages beyond a short distance from the site of its generation. Illustrative active species include singlet oxygen, hydrogen peroxide, NADH, and hydroxyl radicals, phenoxy radical, superoxide and the like. Illustrative quenchers for active species that cause oxidation include polyenes, carotenoids, vitamin E, vitamin C, amino acid-pyrrole N-conjugates of tyrosine, histidine and glutathione. See, e.g., Beutner et al., 2000, *Meth. Enzymol.* 319:226-241.

One consideration in designing assays employing a cleavage-inducing moiety and a cleavable linkage is that they not be so far removed from one another when bound to a protein-protein complex that the active species generated by the cleavage-inducing moiety cannot efficiently cleave the cleavable linkage. In one aspect, cleavable linkages preferably are within about 1000 nm and preferably within about 20-200 nm, of a bound cleavage-inducing moiety. More preferably, for photosensitizer cleavage-inducing moieties generating singlet oxygen, cleavable linkages are within about 20-100 nm of a photosensitizer in a receptor complex. The range within which a cleavage-inducing moiety can effectively cleave a cleavable linkage (that is, cleave enough molecular tag to generate a detectable signal) is referred to herein as its "effective proximity." One of ordinary skill in the art will recognize that the effective proximity of a particular sensitizer may depend on the details of a particular assay design and may be determined or modified by routine experimentation.

A sensitizer is a compound that can be induced to generate a reactive intermediate, or species, usually singlet oxygen. Preferably, a sensitizer used in accordance with the invention is a photosensitizer. Other sensitizers included within the scope of the invention are compounds that on excitation by heat, light, ionizing radiation or chemical activation will release a molecule of singlet oxygen. The best known members of this class of compounds include the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen. Further sensitizers are disclosed by Di Mascio et al., 1994, *FEBS Lett.* 355:287; and Kanofsky, 1983, *J. Biol. Chem.* 258:5991-5993; Pierlot et al., 2000, *Meth. Enzymol.* 319:3-20.

Photosensitizers may be attached directly or indirectly, via covalent or non-covalent linkages, to the binding agent of a class-specific reagent. Guidance for constructing such compositions, particularly for antibodies as binding agents are available in the literature, e.g., in the fields of photodynamic therapy, immunodiagnostics, and the like. Exemplary guidance may be found in Ullman et al., 1994, *Proc. Natl. Acad. Sci. USA* 91, 5426-5430; Strong et al., 1994, *Ann. New York Acad. Sci.* 745: 297-320; Yarmush et al., 1993, *Crit. Rev. Therapeutic Drug Carrier Syst.* 10: 197-252; and U.S. Pat. Nos. 5,340,716, 5,516,636, 5,709,994, and 6,251,581.

In some instances, the cleavage of the molecular tag by the cleavage inducing moiety is induced by light induction. A large variety of light sources are available to photo-activate photosensitizers to generate singlet oxygen. Both polychromatic and monochromatic sources may be used as long as the source is sufficiently intense to produce enough singlet oxygen in a practical time duration. The length of the irradiation depends on the nature of the photosensitizer, the nature of the cleavable linkage, the power of the source of irradiation and its distance from the sample. In general, the period for irradiation may be more than about a microsecond to as long as about 10 minutes, usually in the range of about one millisecond to about 60 seconds. The intensity and length of irradiation should be sufficient to excite at least about 0.1% of the photosensitizer molecules, usually at least about 30% of the photosensitizer molecules and preferably, substantially all of the photosensitizer molecules. Exemplary light sources include lasers such as, e.g., helium-neon lasers, argon lasers, YAG lasers, He/Cd lasers and ruby lasers; photodiodes; mercury, sodium and xenon vapor lamps; incandescent lamps such as, e.g., tungsten and tungsten/halogen and flashlamps. An exemplary photoactivation device suitable for use in the methods of the invention is disclosed International Patent Publication No. WO 03/051669. In such embodiments, the photoactivation device is an array of light emitting diodes (LEDs) mounted in housing that permits the simultaneous illumination of all the wells in a 96-well plate.

Examples of photosensitizers that may be utilized in the present invention are those that have the above properties and those disclosed by U.S. Pat. Nos. 5,536,834, 5,763,602, 5,565,552, 5,709,994, 5,340,716, 5,516,636, 6,251,581, and 6,001,673; published European Patent Application No. 0484027; Martin et al., 1990, *Methods Enzymol.* 186:635-645; and Yarmush et al., 1993, *Crit. Rev. Therapeutic Drug Carrier Syst.* 10:197-252. As with sensitizers, in certain embodiments, a photosensitizer may be associated with a solid phase support by being covalently or non-covalently attached to the surface of the support or incorporated into the body of the support. In general, the photosensitizer is associated with the support in an amount necessary to achieve the necessary amount of singlet oxygen. Generally, the amount of photosensitizer is determined empirically according to routine methods.

In conducting the described methods, a combination of the assay components is made, including the sample being tested and the antibody binding compound. Generally, assay components may be combined in any order. In certain applications, however, the order of addition may be relevant. For example, one may wish to quantitatively monitor competitive binding. Or one may wish to monitor the stability of an assembled complex. In such applications, reactions may be assembled in stages.

The amounts of each reagent can generally be determined empirically. The amount of sample used in an assay will be determined by the predicted number of target complexes present and the means of separation and detection used to monitor the signal of the assay. In general, the amounts of the binding compounds and the cleaving probe can be provided in molar excess relative to the expected amount of the target molecules in the sample, generally at a molar excess of at least about 1.5, more desirably about 10-fold excess, or more. In specific applications, the concentration used may be higher or lower, depending on the affinity of the binding agents and the expected number of target molecules present on a single cell. Where one is determining the effect of a chemical compound on formation of protein complexes on the cell surface, the compound may be added to the cells prior to, simultaneously with, or after addition of the probes, depending on the effect being monitored.

The assay mixture can be combined and incubated under conditions that provide for binding of the probes to the cell surface molecules, usually in an aqueous medium, generally at a physiological pH (comparable to the pH at which the cells are cultures), maintained by a buffer at a concentration in the range of about 10 to 200 mM. Conventional buffers may be used, as well as other conventional additives as necessary, such as salts, growth medium, stabilizers, etc. Physiological and constant temperatures are normally employed. Incubation temperatures normally range from about 4° to 70° C., usually from about 15° to 45° C., more usually about 25° to 37° C.

After assembly of the assay mixture and incubation to allow the probes to bind to cell surface molecules, the mixture can be treated to activate the cleaving agent to cleave the tags from the binding compounds that are within the effective proximity of the cleaving agent, releasing the corresponding tag from the cell surface into solution. The nature of this treatment will depend on the mechanism of action of the cleaving agent. For example, where a photosensitizer is employed as the cleaving agent, activation of cleavage can comprise irradiation of the mixture at the wavelength of light appropriate to the particular sensitizer used.

Following cleavage, the sample can then be analyzed to determine the identity of tags that have been released. Where an assay employing a plurality of binding compounds is employed, separation of the released tags will generally precede their detection. The methods for both separation and detection are determined in the process of designing the tags for the assay. A preferred mode of separation employs electrophoresis, in which the various tags are separated based on known differences in their electrophoretic mobilities.

As mentioned above, in some embodiments, if the assay reaction conditions may interfere with the separation technique employed, it may be necessary to remove, or exchange, the assay reaction buffer prior to cleavage and separation of the molecular tags. For example, assay conditions may include salt concentrations (e.g., required for specific binding) that degrade separation performance when molecular tags are separated on the basis of electrophoretic mobility. Thus, such high salt buffers may be removed, e.g., prior to cleavage of molecular tags, and replaced with another buffer suitable for electrophoretic separation through filtration, aspiration, dilution or other means.

Measuring PD-1-PD-L1 Interactions

An exemplary protein-protein interaction that may be detected using the methods provided herein is the interaction between T cells that express programmed death 1 ("PD-1") and cancer cells that express PD ligand 1 ("PD-L1"). As set forth above, there are several other similar protein-protein complexes that occur between T cells and antigen presenting cells such as cancer cells. The discussion in this section focuses on the PD-1-PD-L1 interaction as an example. It is understood that other such complexes may be detected and measured similarly and used for similar purposes.

A PD-1-PD-L1 interaction occurs between a PD-1 expressing T-cell and PD-L1 expressing tumor cell. The interaction between tumors expressing PD-L1 and PD-1-expressing T-cells reduces the immune response to tumors. (See generally Chen, D. S. and Mellman, I., Oncology meets immunology: the cancer-immunity cycle. *Immunity* 39:1-10 (2013); Keir, M. E., et al., PD-1 and its ligands in tolerance and immunity. *Ann. Rev. Immunol.* 26:677-704 (2008); Teng, M W L, et al., Classifying cancers based on T-cell infiltration and PD-L1. *Cancer Res.* 75:2139-2145 (2015).) Inhibition of the interaction between PD-1 and PD-L1 may restore T-cell anti-tumor activity. Checkpoint inhibitors, such as therapeutic antibodies which bind either PD-1 or PD-L1 and inhibit their interaction are, in clinical development. Immunohistochemistry (IHC) has been used as a biomarker assay for PD-1 or PD-L1. However, to date, IHC status does not definitely indicate responsiveness. For example, not all IHC positive patients respond to anti-PD-1 or anti-PD-L1 therapy, while some IHC negative patients do respond.

There are several drawbacks to using IHC as a biomarker assay for PD-1 and PD-L1. There are multiple IHC methods and reagents that are not standardized and there is not a standard expression level that is identified as "positive" for expression of these proteins. In addition, quantitation by IHC is subjective due to the visual scoring system. The lack of a standard IHC assay may be at least partially responsible for the observed clinical response in IHC negative patients.

In one aspect of the disclosure, accurate quantification of a protein-protein complex interaction between PD-1 and PD-L1 may be a better predictor than either PD-1 or PD-L1, alone or together, for patients likely to respond to anti-PD-1 or anti-PD-L1 therapy. As such, provided are methods for the detection of an interaction between PD-1 and PD-L1 and determining if a patient may respond to anti-PD-1 or anti-PD-L1 therapy.

As described herein, the interaction of PD-1 and PD-L1 expressed on different cells may be detected using a VeraTag® assay having a format described in this disclosure. In particular, the complex is detected based on proximity-dependent release of a VeraTag® reporter molecule that occurs inter-cellularly (between proteins on different cells). Detection of signal using this type of assay is dependent on the close proximity of two cells, a T-cell and a tumor cell. The PD-1-PD-L1 VeraTag® assay methods described in this disclosure produce a direct quantitative and continuous measurement of the amount of PD-1-PD-L1 complex over a wide dynamic range.

For example, PD-1-PD-L1 complex formation can be detected using a proximity-dependent, light release VeraTag® assay format in which a VeraTag® reporter molecule is attached to an anti-PD-1 antibody and is paired with a biotinylated anti-PD-L1 antibody. In another example, PD-1-PD-L1 complex formation can be detected using a proximity-dependent, light release VeraTag® assay format in which a VeraTag® reporter molecule is attached to an anti-PD-L1 antibody and is paired with a biotinylated anti-PD-1 antibody. The schematic diagram shown in FIG. 1F and FIG. 1G is representative of both of these assay formats. In another example, PD-1-PD-L1 complex formation can be detected using a proximity-dependent, light release VeraTag® assay format in which a VeraTag® reporter molecule is attached to a secondary antibody that binds to an anti-PD-L1 antibody and is paired with a biotinylated anti-PD-1 antibody. In another example, PD-1-PD-L1 complex formation can be detected using a proximity-dependent, light release VeraTag® assay format in which a VeraTag® reporter molecule is attached to a secondary antibody that binds to an anti-PD-1 antibody and is paired with a biotinylated anti-PD-L1 antibody. The schematic diagram shown in FIG. 1H is representative of both of these assay formats. In another example, PD-1-PD-L1 complex formation can be detected using a proximity-dependent, light release VeraTag® assay format in which a VeraTag® reporter molecule is attached to a first secondary antibody that binds to an anti-PD-L1 antibody and is paired with a biotinylated secondary antibody that binds to an anti-PD-1 antibody. In another example, PD-1-PD-L1 complex formation can be detected using a proximity-dependent, light release VeraTag® assay format in which a VeraTag® reporter molecule is attached to a first secondary antibody that binds to an anti-PD-1 antibody and is paired with a biotinylated secondary antibody that binds to an anti-PD-L1 antibody. The schematic diagram shown in FIG. 1I is representative of both of these assay formats.

In some instances, the PD-L1 antibody used in the methods described herein may be rabbit anti-human PD-L1 monoclonal antibody E1L3N (Cell Signaling) or rabbit anti-human PD-L1 monoclonal antibody 28-8 (Abcam, catalog #ab205921). In some instances, the PD-1 antibody used in the methods described herein may be any of the antibodies listed in Table 2. The molecular tag employed in the assays described herein may be any of the tags described in U.S. Pat. Nos. 6,627,400; 7,105,308; 7,255,999; 9,110, 975; 7,402,397; and 8,357,277.

Figure 7:
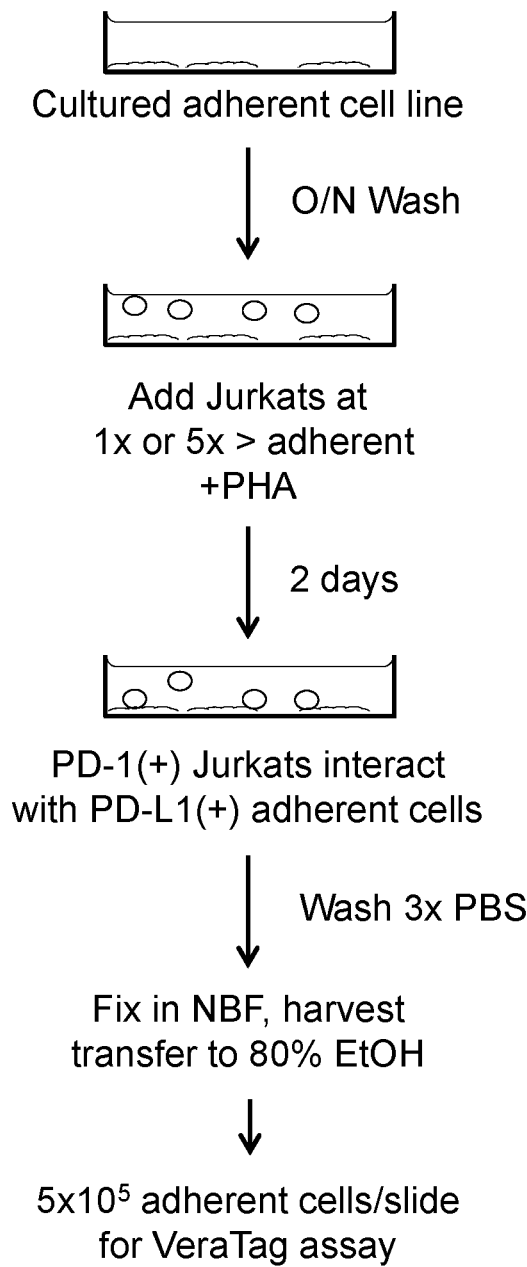
FIG. 7 is a schematic diagram showing a co-culture procedure with Jurkat and adherent cell lines used to make cell line controls for the PD-1-PD-L1 VeraTag® assay according to some aspects of the disclosure. The adherent cell lines are cultured overnight, washed and PHA stimulated Jurkat cells are added to the culture at 1- or 5-fold excess over the adherent cell line. The co-cultures are grown for two days and then washed 3-time with cold PBS. The final wash step removes unattached Jurkat cells from the co-culture dish. Cells are then fixed with NBF overnight and then transferred to 80% ethanol and stored at 4° C.

In some instances, the protein-protein interaction between PD-1 and PD-L1 may be detected in a cell culture system in which adherent cancer cells are co-cultured with an immortalized line of T lymphocyte cells such as Jurkat cells, as described with respect to FIG. 7. The adherent cell lines may be cultured overnight, washed, and then PHA stimulated Jurkat cells may be added to the culture at 1:1 or in excess over the adherent cell line (such as 2×, 5×, 10×). The co-cultures may be grown for 1, 2, 3, 4, or 5 days and then washed to remove unbound cells (expected to be primarily the lymphocyte cells). The co-cultured cells may then be fixed prior to analysis. A similar assay format may readily be employed to assess the protein interactions of other checkpoint inhibitor proteins expressed on cancer cells. In some instances, this assay format may be used to assess the ability of a test compound, such as a chemical compound, a peptide, or an antibody or antibody fragment, to alter the interaction between the two target proteins, thereby facilitating the identification of a therapeutic molecule. Such assays may be used as a screening assay to test different test molecules. In some instances, the test molecule may be an inhibitor of the protein-protein interaction, reducing the interaction between the target proteins. For example, the target molecule may bind to a portion of one of the target proteins in the same region that the other target protein interacts with. In some instances, the test molecule may be a stimulatory molecule that promotes the protein-protein interaction of the target proteins.

In another aspect, provided is a method of screening test agents for the ability to disrupt or promote formation of a protein-protein interaction between two cells in a sample, the method having the steps of: (a) contacting a test cell culture with a test agent, the test cell culture comprising a first cell expressing a first protein on its cell surface and a second cell expressing a second protein on its cell surface; (b) measuring the amount of protein-protein interaction between the first protein and the second protein using any of the methods described above; and (c) comparing the amount of protein-protein interaction measured in step (b) to the amount of protein-protein interaction measured between the first protein and the second protein in a control cell culture not contacted with the test agent, the control cell culture comprising the first cell expressing the first protein on its cell surface and the second cell expressing the second protein on its cell surface.

In some instances, the test agent may be an inhibitor of the protein-protein interaction between the first protein and the second protein if the amount of protein-protein interaction is decreased in the test cell culture as compared to the control cell culture. In other instances, the test agent may be a promoter of the protein-protein interaction between the first protein and the second protein if the amount of protein-protein interaction is increased in the test cell culture as compared to the control cell culture.

In some instances, the first cell and the second cell may be different cell types. In some instances, the first cell and the second cell may be different cancer cell lines. In some instances, one of the first cell and the second cell in an adherent cell line and the other is a non-adherent cell line. In some instances, the first cell is a Jurkat cell and the second cell is an adherent cancer cell.

Figure 2A:
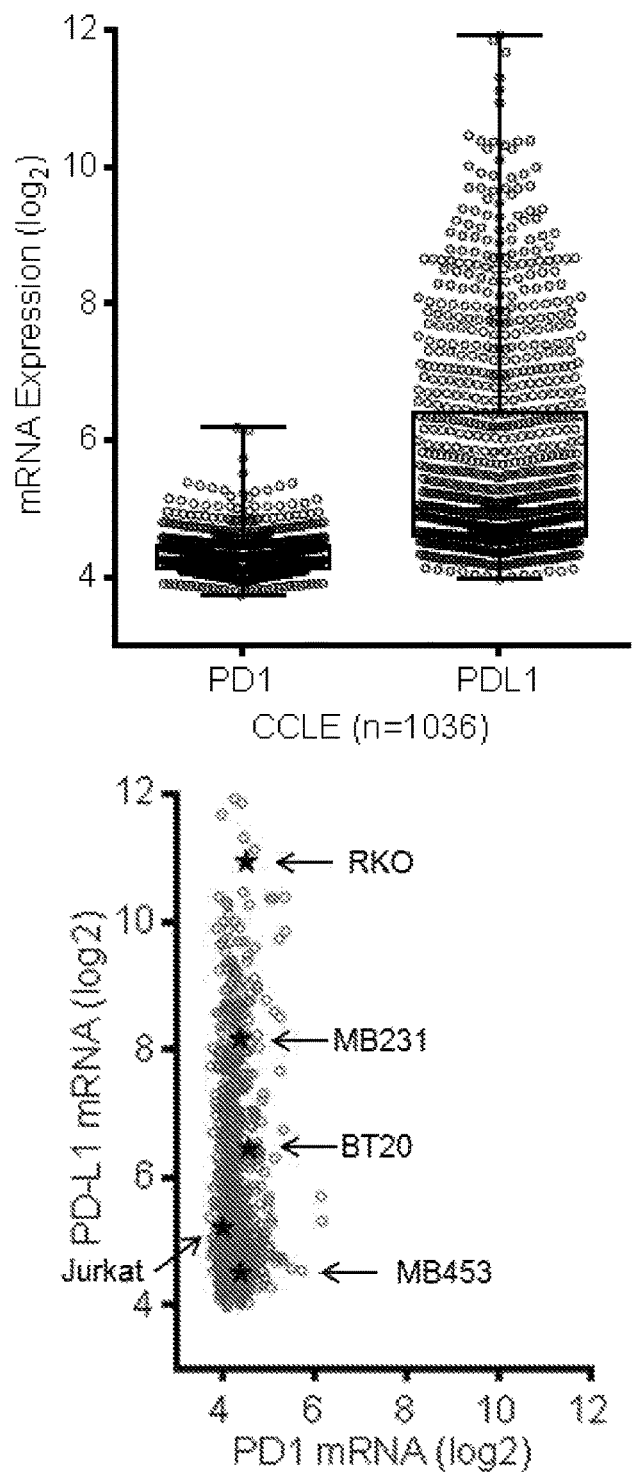
FIG. 2A shows scatter plot distributions illustrating the relationship between mRNA expression levels of PD-1 and PD-L1 from 1036 cell lines in the Cancer Cell Line Encyclopedia (CCLE, data available at www.broadinstitute.org/ccle/home) according to some aspects of the disclosure. PD-L1 mRNA levels show a dynamic range of ~250-fold, while PD-1 mRNA levels are much less variable, having a dynamic range of approximately 5-fold. In the top graph, the PD-1 and PD-L1 mRNA expression levels were plotted separately on the x-axis, while the bottom graph shows this data re-plotted against each other. The five cell lines used in the examples described in this disclosure are indicated by stars. They were chosen to represent the wide dynamic range of PD-L1 mRNA expression, reflective of the entire CCLE population of cell lines.
Figure 2B:
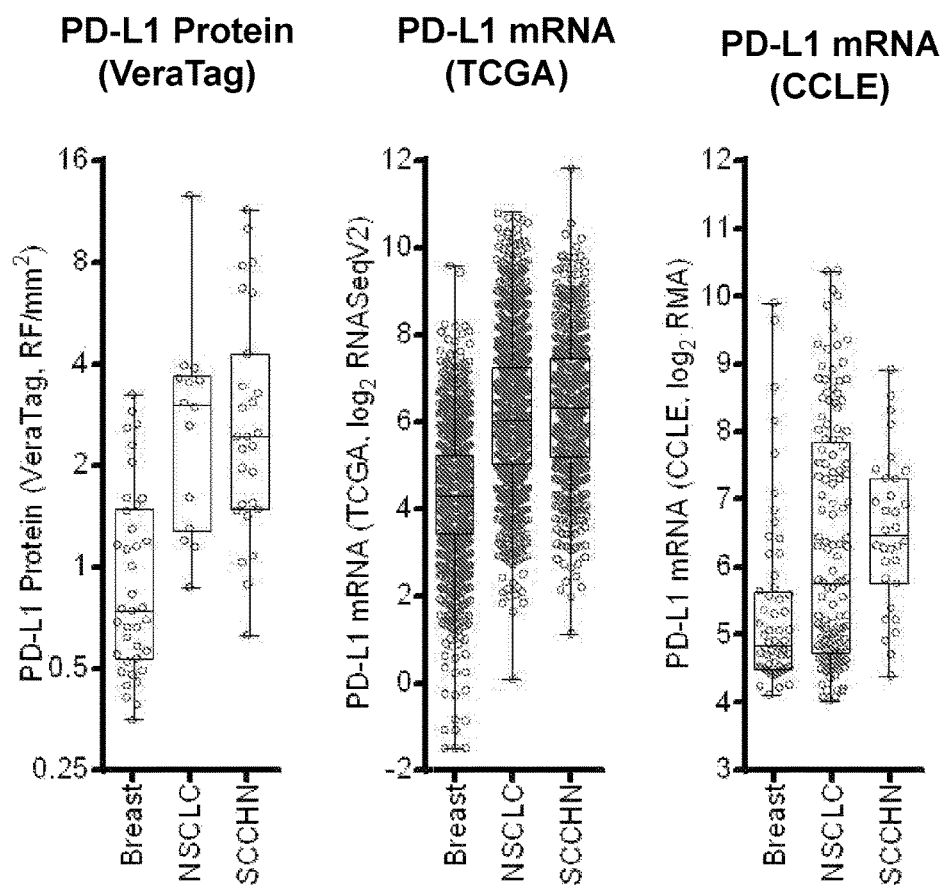
FIG. 2B shows scatter plots comparing the PD-L1 expression levels between breast cancer, non-small cell lung cancer (NSCLC), and squamous cell carcinoma of the head and neck (SCCHN) based on protein measurements obtained using the VeraTag® assay and mRNA measurements obtained from The Cancer Genome Atlas (TCGA) and CCLE according to some aspects of the disclosure. The samples analyzed using the VeraTag® assay were obtained from Asterand Bioscience (n=38; NSCLC, n=14; SCCHN, n=27). TCGA includes data from the following tumor samples: n=1,100; NSCLC, n=1,018; SCCHN, n=522. CCLE includes data from the following cell lines: n=59; NSCLC, n=133; SCCHN, n=32. There is a statistically different lower levels of PD-L1 protein as measured by the VeraTag® assay in breast cancer than in either lung-NSC or SCCHN ($p<0.0001$ for breast vs. NSCLC or SCCHN). These differences are consistent with the PD-L1 mRNA levels from tumors (TCGA) ($p<0.0001$ for breast vs. NSCLC or SCCHN) and cell lines (CCLE) ($p<0.0001$ for breast vs. SCCHN, $p<0.0002$ for breast vs. NSCLC).
Figure 8A:
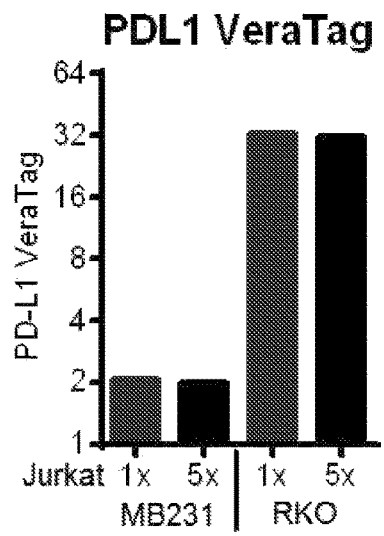
FIG. 8A-8C shows bar graphs plotting the amount of PD-1, PD-L1, and PD-1-PD-L1 complex as measured by VeraTag® assay in two different cell lines (MD-MBA-231 and RKO) co-cultured as described in FIG. 7 with either 1× or 5× amounts of Jurkat cells according to some aspects of the disclosure. The amount of protein or protein complex detected (y-axis) is plotted as relative peak area (RPA) for each cell line at each ratio of Jurkat cells (x-axis). The assay formats used for these experiments are schematically shown in FIG. 1E (PD-1 and PD-L1) and FIG. 1I (PD-1-PD-L1 complex).
Figure 8B:
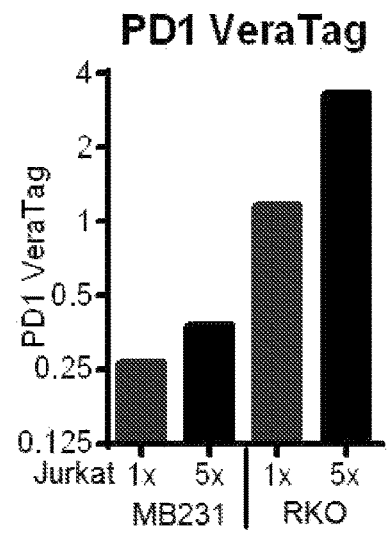
Figure 8C:
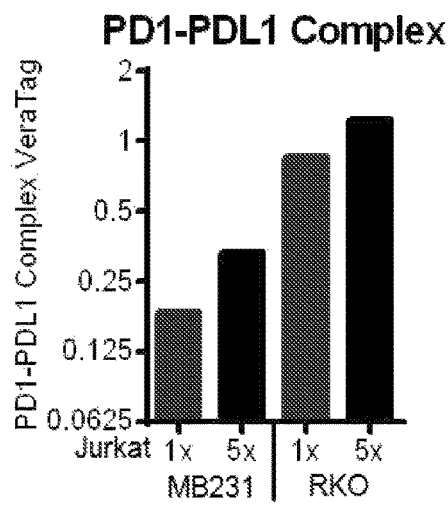
Figure 10A:
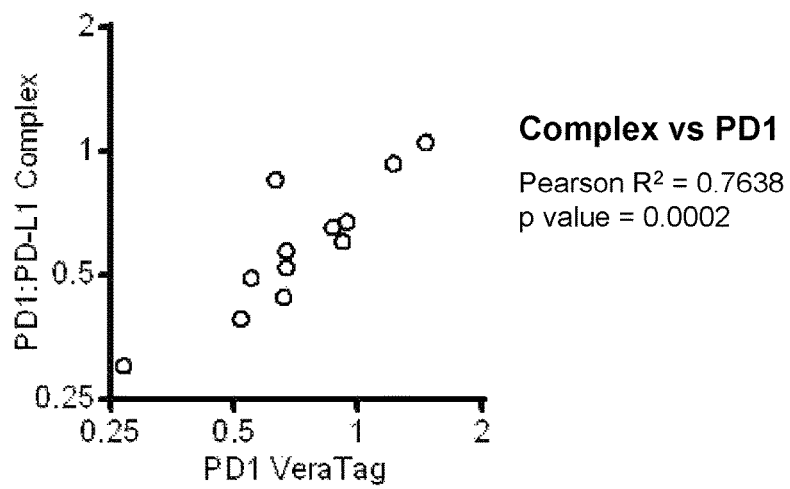
FIGS. 10A-10C shows graphs illustrating pair wise comparisons of PD1:PD-L1 complex level to PD-1 expression, PD1:PD-L1 complex level to PD-L1 expression, and PD-L1 expression to PD-1 expression as measured by VeraTag® assays, respectively, according to some aspects of the disclosure. PD-1 data and PD-1-PD-L1 complex data is from the analysis shown in FIG. 9A and FIG. 9B, respectively. Pearson correlation coefficient and p-value for each comparison is shown.
Figure 10B:
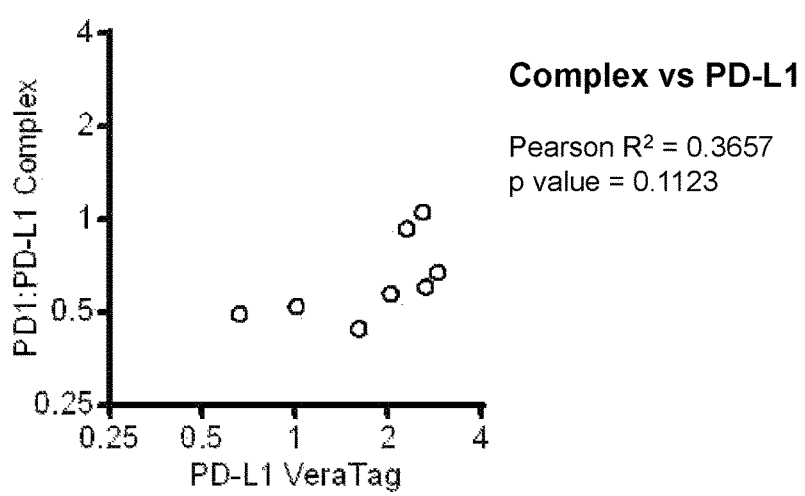
Figure 10C:
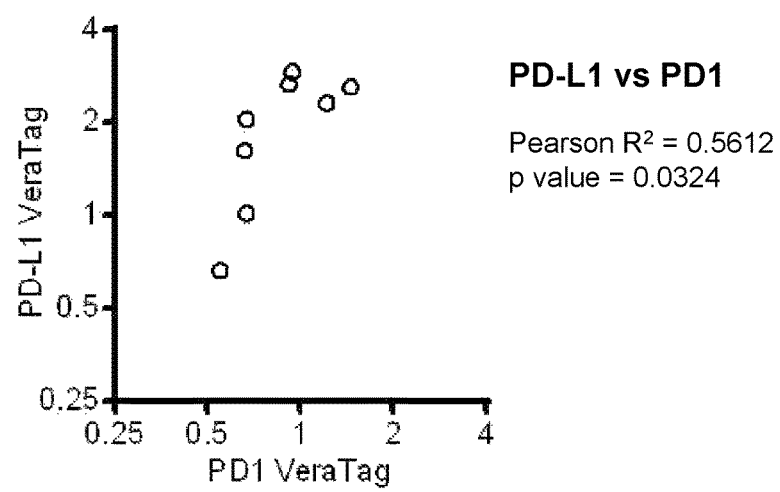

In some instances, the amount of PD-L1 protein and PD-1 protein detectable using the methods described herein is proportional to the amount of mRNA expression of these proteins as described, for example, in FIG. 2B. In some instances, the amount of PD-1-PD-L1 complex detectable using the methods described herein increases as the amount of PD-L1 mRNA in the sample increases as shown, for example, in FIG. 8D. In other instances, the amount of complex detected may increase as the amount of PD-1 mRNA increases in the sample. These embodiments are illustrated in FIGS. 8A-8C in which the amount of PD-1 protein in the sample detected by the provided methods increases as the amount of Jurkat cells with which the adherent cancer cell lines are co-cultured. Also, as shown in FIGS. 10A-10C, the amount of complex detected by the provided methods is correlated in a statistically significant manner to the amount of PD-1 protein in the samples.

In tumor samples, the detection of PD-1-PD-L1 complex using the described methods may reveal infiltration of a tumor by T cells. In some instances, the amount of PD-1-PD-L1 complex detected with the described assays in a tumor sample from a patient may be predictive of a patient's likelihood to respond to anti-PD-1 or anti-PD-L1 therapy. In some instances, the amount of PD-1-PD-L1 complex detected with the described assays in a tumor sample from a patient may correlate with the patient's likelihood to respond to anti-PD-1 or anti-PD-L1 therapy.

In one aspect, provided is a method for predicting responsiveness of a subject having a cancer to an immune checkpoint targeted therapy comprising: (a) measuring the amount of a checkpoint molecule-ligand complex in a biological sample from the subject's cancer using a method of quantitating protein-protein interaction as described in this disclosure; (b) determining whether the amount of the complex in the subject's sample is above or below a threshold level; and (c) indicating that the subject is more likely to respond to the checkpoint targeted therapy if the amount of the complex in the subject's sample is equal to or above the threshold level than if the amount of the complex is below the threshold level.

In one aspect, provided is a method for predicting responsiveness of a subject having a cancer to a PD-1 or PD-L1 acting agent comprising: (a) measuring the amount of PD-1-PD-L1 complex in a biological sample from the subject's cancer using a method of quantitating protein-protein interaction as described in this disclosure; (b) determining whether the amount of PD-1-PD-L1 complex in the subject's sample is above or below a threshold level; and (c) indicating that the subject is more likely to respond to the PD-1 or PD-L1 acting agent if the amount of PD-1-PD-L1 complex in the subject's sample is equal to or above the threshold level than if the amount of PD-1-PD-L1 complex is below the threshold level.

In some instances, the amount of the first protein, the second protein, or both, may be determined in addition to quantitation of the amount of complex between the two proteins. In some instances, the method involves quantitating the amount of the first protein to determine the amount of T cell infiltration in the tumor. For example, if there is a large amount of the first protein present, it may indicate that there are large numbers of activated T cells infiltrating the tumor. In another example, if there is a small amount of the first protein present, it may indicate that there are few activated T cells present in the tumor. In some instances, the responsiveness of a patient to a therapy directed to the first protein or the second protein (for example, in terms of how quickly the patient responds to such therapy) may be increased where there is a large number of activated T cells present in the tumor.

As used herein, the terms "subject" and "patient" are used interchangeably. As used herein, the terms "subject" and "subjects" refer to an animal, preferably a mammal including a non-primate (e.g., a cow, pig, horse, donkey, goat, camel, cat, dog, guinea pig, rat, mouse, sheep) and a primate (e.g., a monkey, such as a cynomolgous monkey, gorilla, chimpanzee and a human).

In some instances, the threshold level is a median amount of PD-1-PD-L1 complex determined in a reference population of patients having the same kind of cancer as the subject. In another instance, the threshold level is an optimal amount of PD-1-PD-L1 complex determined in a reference population of patients having the same kind of cancer as the subject. "Optimal cutoff as used herein, refers to the value of a predetermined measure on subjects exhibiting certain attributes that allow the best discrimination between two categories of an attribute. For example, finding a value for an optimal cutoff that allows one to best discriminate between two categories (subgroups) of patients for determining overall survival. Optimal cutoffs are used to separate the subjects with values lower than or higher than the optimal cutoff to optimize the prediction model, for example, without limitation, to maximize the specificity of the model, maximize the sensitivity of the model, maximize the difference in outcome, or minimize the p-value from hazard ratio or a difference in response.

"Responsiveness," to "respond" to treatment, and other forms of this verb, as used herein, refer to the reaction of a subject to treatment with a Her-2-acting agent. As an example, a subject responds to treatment with a PD-1 acting agent or PD-L1 acting agent if growth of a tumor in the subject is retarded about 10%, 20%, 30%, 40%, 50%, 60%, 70%, 80%, 90% or more. In another example, a subject responds to treatment with a Her-2-acting agent if a tumor in the subject shrinks by about 5%, 10%, 20%, 30%, 40%, 50% or more as determined by any appropriate measure, e.g., by mass or volume. In another example, a subject responds to treatment with a PD-1 acting agent or PD-L1 acting agent if the subject experiences a life expectancy extended by about 5%, 10%, 20%, 30%, 40%, 50% or more beyond the life expectancy predicted if no treatment is administered. In another example, a subject responds to treatment with a PD-1 acting agent or PD-L1 acting agent if the subject has an increased disease-free survival, overall survival or increased time to progression. Several methods may be used to determine if a patient responds to a treatment including overall survival rate, time to progression, progression free survival, and/or using the RECIST criteria or other medically accepted response criteria. The RECIST criteria, stands for "Response Evaluation Criteria in Solid Tumours" criteria, and is a set of published rules that define when cancer patients improve ("respond"), stay the same ("stable") or worsen ("progression") during treatments. Response as defined by RECIST criteria have been published, for example, at *Journal of the National Cancer Institute*, Vol. 92, No. 3, Feb. 2, 2000. These guidelines are updated periodically and any such updates are contemplated within the scope of this disclosure. It is also contemplated that criteria, rules, or guidelines other than the RECIST criteria may developed in the future to characterize clinical tumor response, and any such criteria, rules, or guidelines are contemplated within the scope of this disclosure. One skilled in the art would understand definitions that go with RECIST criteria including partial response ("PR"), complete response ("CR"), stable disease ("SD"), and progressive disease ("PD").

EXAMPLES

The present invention may be better understood by reference to the following nonlimiting examples.

Example 1. Antibodies, VeraTag®-Antibody, Biotin, and Molecular Scissors

A monoclonal antibody recognizing the intracellular domain of human PD-L1 was purchased from Cell Signaling Technologies (rabbit anti-human PD-L1 monoclonal antibody E1L3N). Other anti-human PD-L1 antibodies would be suitable in the assays described herein if compatible for use with FFPE samples, such as commercially available rabbit anti-human PD-L1 monoclonal antibody 28-8 (Abcam, catalog #ab205921). Table 2 below shows the ten anti-human PD-1 antibodies that were studied, as well as their isotype and immunogen (rhPD-1 refers to recombinant human PD-1).

TABLE 2

Anti-human PD-1 mouse monoclonal antibodies tested

| Clone Name (type) | Isotype | Immunogen | Vendor (Catalog #) |
|---|---|---|---|
| NAT105 (mouse monoclonal) | IgG1 | intracellular domain | Cell Marque (315M-95) |
| UMAB198 (mouse monoclonal) | IgG2a | Full length rhPD-1 | OriGene (UM800090) |
| 7A11B1 (mouse monoclonal) | IgG1 | N' terminal 150 aa of rhPD-1 | ThermoFisher Scientific (MA5-15780) |
| 12A7D7 (mouse monoclonal) | IgG1 | N' terminal 150 aa of rhPD-1 | ThermoFisher Scientific (MA5-15781) |
| J121 (mouse monoclonal) | IgG1 | unknown | eBioscience (14-2798) |
| EH33 (mouse monoclonal) | IgG2a | N' terminus of rhPD-1 | Cell Signaling Technologies (43248) |
| EH12.2H7 (mouse monoclonal) | IgG1 | unknown | BioLegend (329902) |
| J116 (mouse monoclonal) | IgG1 | unknown | eBioscience (16-9989-82) |
| UMAB199 (mouse monoclonal) | IgG2a | Full length rhPD-1 | OriGene (UM800091) |
| AF1086 (goat polyclonal) | IgG | Leu25-Gln167 of rhPD-1 | R&D Systems (AF1086) |

VeraTag® reporter molecules Pro11 and Pro125 (FIG. 1J) and streptavidin-conjugated methylene blue ("molecular scissors") were synthesized and purified according to the protocol described previously in U.S. Pat. No. 7,105,308, which is incorporated by reference herein, including any drawings. Antibody-biotin conjugates were made using sulfo-NHS-LC-LC-biotin (Pierce) as a linker according to manufacturer's protocol, and antibody-biotin and antibody-tag conjugation products were purified by HPLC (Agilent) or 1 cm×10 cm Sephadex G-50 size-exclusion column on an AKTA FPLC (GE Healthcare Life Sciences). In certain experiments, the VeraTag® reporter molecule or biotin was conjugated to a primary antibody, such as shown in FIGS. 1C, 1F, 1G, and 1H. In other experiments, the VeraTag® tag or biotin was conjugated to a secondary antibody that binds to the primary antibody, such as shown in FIGS. 1D, 1E, 1H, and 1I.

Example 2. Cell Culture

All cell lines were maintained at 37° C., 5% $CO_2$ in Gibco's RPMI 1640 with L-glutamine growth medium supplemented with, 10% fetal bovine serum (FBS) and penicillin (100 U/mL) and streptomycin (100 ug/mL). All cell lines were purchased from American Type Culture Collection (ATCC).

Example 3. Culture and Stimulation of Jurkat Cell Line

Jurkat cells were cultured at 1 to $2\times10^6$ cells/mL in 100 mL of medium in T-175 cell culture flasks (Corning). For stimulation, phytohemagglutinin-L (PHA-L, Roche) was added at a final concentration of 3 µg/mL and incubated at 37° C., 5% $CO_2$ for 2 days. Cells were harvested by centrifugation at 300×g for 10 mins at 4° C., followed by 2 washes with cold PBS. To fix cells, cell pellets were resuspended in 20 mL of 10% neutral buffered formalin (10% NBF, Richard-Allen Scientific) and placed on a rotisserie at 4° C. overnight (>16 hrs). Cells were centrifuged at 300×g for 10 min, the fixation solution was removed, and the cell pellet was re-dissolved in a minimal amount of 80% ethanol (3 to 4 mL) and stored at 4° C.

Example 4. Co-Culturing Adherent and Jurkat Cell Lines

Each of adherent cells lines MDA-MB453, BT-20, MDA-MB231, and RKO were co-cultured with suspension Jurkat T-cells. An outline of this co-culture experiment is shown in FIG. 7. Adherent cell lines were seeded at $10\times10^6$ cells with 20 mL medium in 150 mm culture dishes (approximately 50% confluency) and allowed to adhere overnight. The following day the medium was removed and the cells were washed once with cold phosphate buffered saline (PBS, Gibco). Jurkat cells were slowly added to the adherent cell lines at either $5\times10^5$ cells/mL or $2.5\times10^6$ cells/mL in 20 mL of medium, $10\times10^6$ or $50\times10^6$ Jurkat cells total (equivalent to 1- or 5-fold greater than the amount of adherent cells; culture condition 1 and 2, respectively), together with 3 µg/mL phytohemagglutinin-L (PHA-L, Roche) and the co-cultures were allowed to grow for 48 hours. After removal of the medium, culture dishes were washed 3 times with cold PBS to remove all nonadherent cells and 20 mL of 10% neutral buffered formalin (10% NBF, Richard-Allen Scientific) was added to the culture dishes for 1 hour at 4° C. to fix cells and immobilize any Jurkat cells interacting with the adherent cell line. Cells were then scraped into a 50 mL centrifuge tube (Corning), 10% NBF was added to 35 mL, and placed on a rotisserie at 4° C. overnight (>16 hrs). The cells were centrifuged at 300×g for 10 min, the fixation solution was removed, and the cell pellet was re-dissolved in a minimal amount of 80% ethanol (1 to 2 mL) and stored at 4° C.

Example 5. Preparation of Slides for VeraTag® Assays

Fixed tissues: Formalin-fixed, paraffin-embedded (FFPE) breast, NSCLC, and SCCHN tissue sample blocks were purchased from Asterand Biosciences. Five micron tissue sections were placed on positively-charged glass slides (Fisherbrane™ Superfrost™ plus microscope slides, catalog number 12-550-15) and then baked in a heated oven set at 70° C. for 20 mins. All sample slides were stored at 4° C. for future assays.

Cultured cells: Fixed cells were diluted to 12,500 or 625 cells/mL in 40% ethanol and 40 µL (500,000 or 25,000 cells in total) were placed on positively charged glass slides (Fisherbrand™ Superfrost™ plus microscope slides, catalog number 12-550-15) and then baked in a heated oven set at 70° C. for 20 mins. All sample slides were stored at 4° C. for future assays.

Example 6. VeraTag® Assay Protocol

1. DTT-Release Assays

Slides (either FFPE tissue samples or cultured cells) were subjected to heat-induced epitope retrieval (HIER) with 250 mL of Diva Decloaker, pH 6.2 (Biocare Medical#DV2004MM) in a Decloaking Chamber™ Pro (Biocare Medical) for 40 minutes at 95° C. and 10 sec at 90° C. Slides were removed from the Decloaking Chamber and allowed to cool for 1 hour at room temperature. The slides were rinsed six times with deionized water and partially dried in a centrifuge (Tomy PMC-082) modified to spin slowly. A hydrophobic circle was drawn around the sample using a mini PAP pen (Invitrogen catalog number 00-8877) to retain reagents on the sample. The samples were then -covered for 1 hr with blocking buffer that contained 10% goat serum (Sigma #G9023) and 1.5% bovine serum albumin in PBS. After removal of the blocking buffer with aspiration, a solution containing the primary antibody in blocking buffer was added to the slides and left at 4° C. overnight in a humidified chamber with gentle shaking. The antibody solution was aspirated and samples were washed with PBS containing 0.25% Triton® X-100 for 5 minutes then PBS for 5 minutes. Following aspiration, the secondary antibody in blocking buffer was added. The secondary antibody was allowed to incubate at room temperature for 1 hour in a humidified chamber. The slides were then transferred to a slide rack in deionized water and then rinsed with PBS containing 0.25% Triton® X-100 for 5 minutes followed by 6 washes with deionized water for 1 minute each. The slides are partially dried in a centrifuge (Tomy PMC-082) and then release buffer containing 1.0 mM dithiothreitol (DTT), 3 pM fluorescein and two CE internal markers (MF and ML) in 0.0 IX PBS was added on the sample sections. Slides were incubated in a humidified chamber for 3 hours to allow for the release of the VeraTag. The release buffer from each slide was transferred to a 96-well plate then diluted appropriately (generally 10-fold) in release buffer not containing DTT. The released VeraTagSup®/Sup reporter molecules in the release buffer were separated and detected on a ABI3130 CE instrument (22-cm capillary array, Applied Biosy stems) under the CE injection condition of 6 kV and 50 sec and run for 650 seconds at 30° C. The identification and quantification of VeraTagSup®/Sup was carried out using VeraTagSup®/Sup Informer software (see, for example, United States publication number 0203408-A1, which is incorporated by reference herein, including any drawings). To analyze the VeraTagSup®/Sup reporter molecule signals in a raw CE electropherogram, two CE internal markers, MF (first marker) and ML (last marker), were used to identify the VeraTagSup®/Sup peaks according to their electrophoretic mobility or migration time (t) relative to the two markers according to the following formula: [t(VeraTag)-t(MF)]/[t(ML)-t(MF)]. The identified VeraTagSup®/Sup peaks were then quantified by peak area calculation for each VeraTag. To correct for variability in VeraTagSup®/Sup recovery from the tissue section, and the run variability in CE injection efficiency and/or detection sensitivity across capillary array, fluorescein (3 pM) was included in the VeraTagSup®/Sup Capture Buffer (CB), and co-electrophoresed as an internal reference control in each sample run. The area of each VeraTagSup®/Sup reporter molecule peak was then reported as relative peak area (RPA) by area normalization of the VeraTagSup®/Sup peak (VeraTagSup®/Sup peak area) to the internal fluorescein peak (fluorescein peak area).

Slides were stained with hematoxylin and eosin (H&E) by standard techniques. Briefly, slides were placed in staining racks and first rinsed in tap water. Slides were serially dipped in hematoxylin, clarifier and bluing agent for 45 seconds each, followed by tap water rinses after each step. Slides were then treated with 5% water in alcohol (2 fresh solutions) then 100% alcohol (3 fresh solutions) then xylene (3 fresh solutions, 5 minutes each). Finally, a coverslip was applied to protect the section.

The final quantification terms for the target protein detected by the VeraTag® assay was calculated as either RPA for similar samples (cell culture samples) using identical Capture Buffer volumes or as the RPA*CB vol/tumor area (in $mm^2$) to account for different amounts of tumor on the slides.

Figure 3:
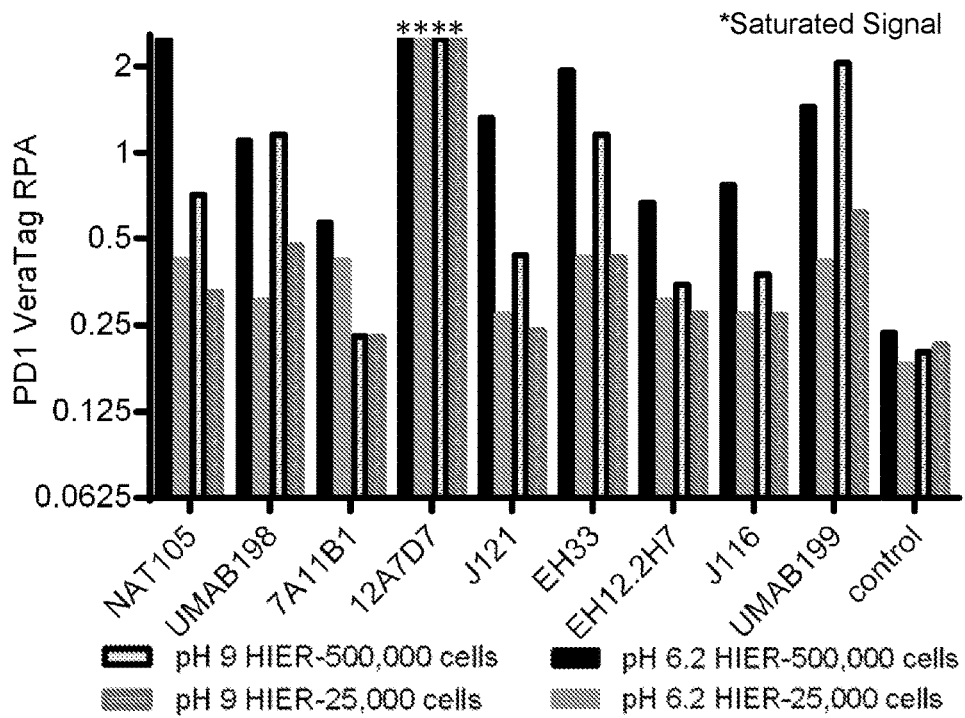
FIG. 3 shows the results of an anti-PD-1 antibody assessment experiment assessing the ability of nine different anti-PD-1 antibodies to detect PD-1 when used in a VeraTag® assay according to some aspects of the disclosure. The assay format used an anti-PD-1 primary and a secondary antibody labeled with a DTT-releasable tag as shown in FIG. 1E. Epitope retrieval was performed with either pH 6.2 or pH 9 heat-induced epitope retrieval (HIER) buffer. The antibodies were tested on 500,000 or 25,000 Jurkat cells stimulated with phytohemagglutinin-L (PHA-L). The amount of PD-1 detected using the antibodies was determined as relative peak area (RPA) ("PD1 VeraTag RPA").
Figure 4:
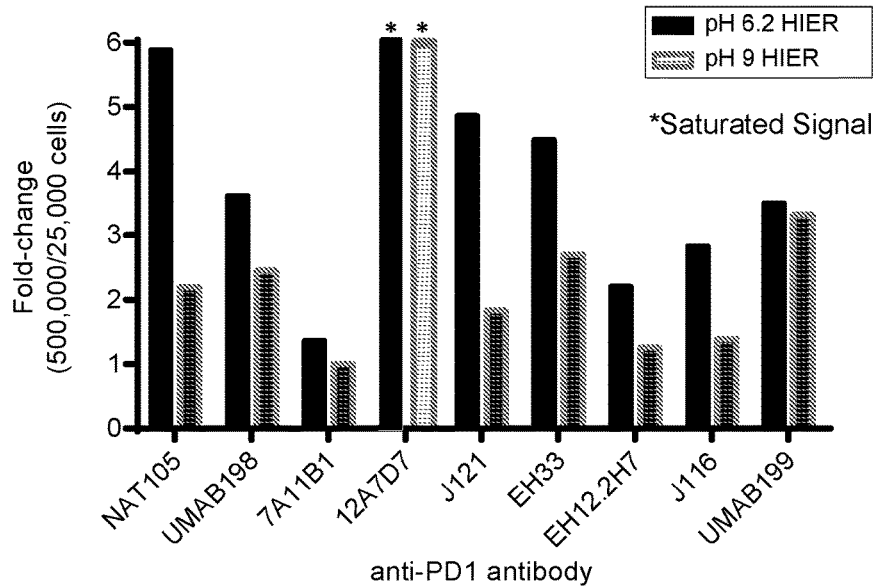
FIG. 4 shows the fold-change in PD-1 detected by VeraTag® assay (RPA) between the 500,000 or 25,000 Jurkat cell experiments described in FIG. 3 according to some aspects of the disclosure.
Figure 5A:
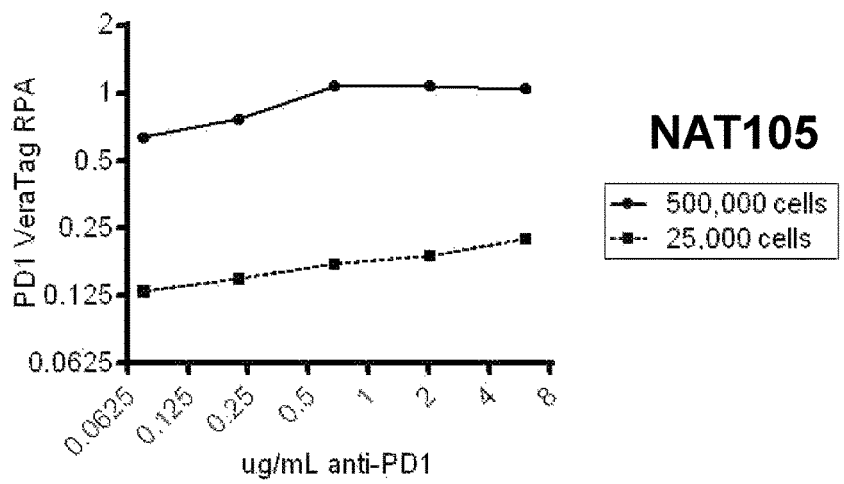
FIGS. 5A-5C show the results of an antibody titration experiment assessing three different anti-PD-1 antibodies in a VeraTag® assay to detect PD-1 in either 500,000 or 25,000 Jurkat cells stimulated with phytohemagglutinin-L (PHA-L) according to some aspects of the disclosure. The assay format used an anti-PD-1 primary antibody and a secondary antibody labeled with a DTT-releasable tag as shown in FIG. 1E. As the amount of antibody used in the assay was increased, an increasing amount of VeraTag® assay signal was detected. X-axes are the antibody concentrations and the y-axes are the VeraTag® assay signal (RPA; "PD-1 VeraTag RPA").
Figure 5B:
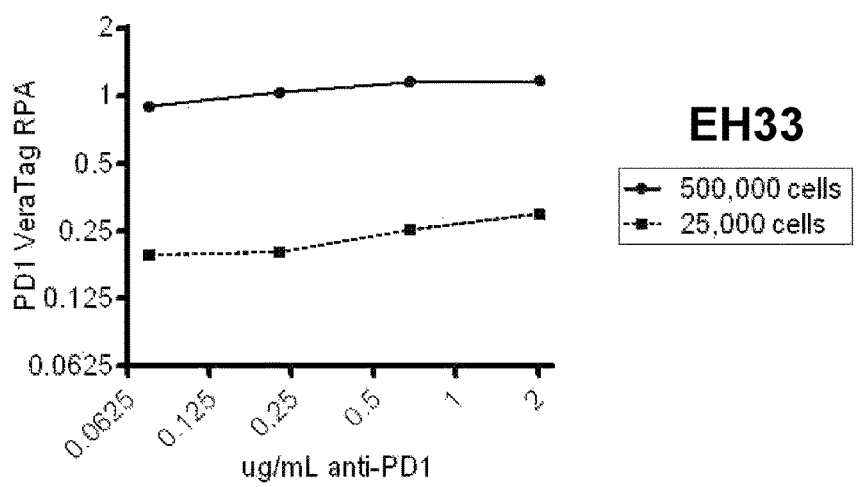
Figure 5C:
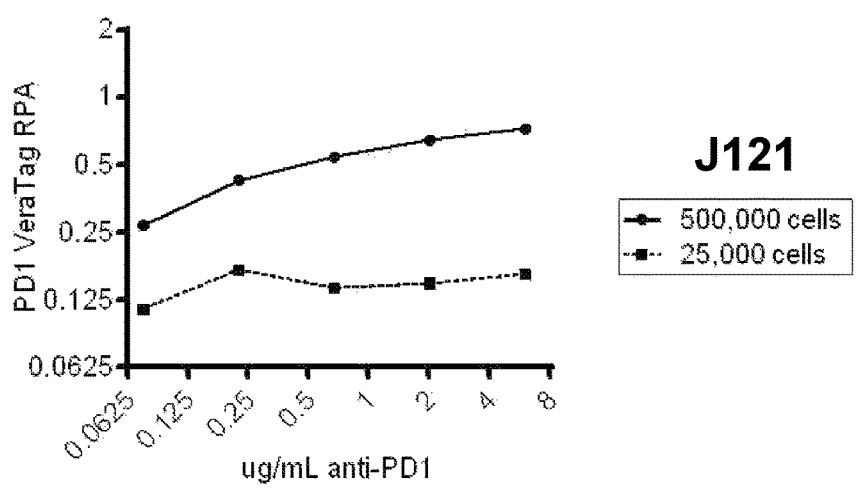

For the experiments described in FIG. 3 and FIG. 4, the same protocol was performed using Target Retrieval Solution, pH 9.0 (Dako Corp., #S2368) in parallel to Diva Decloaker, pH 6.2 (Biocare Medical, #DV2004MM) as the heat-induced epitope retrieval (HIER) buffer so as to compare the two buffers when testing the various PD1 antibodies.

2. Light-Release Assays

The light-release VeraTagSup®/Sup assay format follow the procedure described above for the DTT-release assay format up to and including the addition and incubation of the secondary antibody except that Diva Decloaker, pH 6.2 (Biocare Medical, #DV2004MM) is used as the heat-induced epitope retrieval (HIER) buffer. Following incubation with the secondary antibody, samples were then washed with PBS containing 0.25% Triton® X-100 for 5 minutes then PBS for 5 minutes and aspirated. Following aspiration, streptavidin-conjugated methylene blue at concentration of 2.5 µg/mL in IX PBS was added and allowed to incubate at room temperature for 1 hour in a humidified chamber. The slides were then transferred to a slide rack in deionized water and then rinsed with PBS containing 0.25% Triton® X-100 for 5 minutes followed by 6 washes with deionized water for 1 minute each. The slides are partially dried in a centrifuge (Tomy PMC-082) and then illumination buffer containing 3 pM fluorescein and two CE internal markers (MF and ML) in 0.002×PBS was added on sample sections. The bound VeraTagSup®/Sup was released at ~4° C. by photo-activated cleavage using an in-house high-powered LED array illuminator equipped with an electronic ice cube (Torrey Pine Scientific). After illumination, VeraTagSup®/Sup intermediates were reduced to a quantifiable form by the addition of sodium borohydride. The released VeraTagSup®/Sup reporter molecules in the CE samples were separated and detected on a ABI3130 CE instalment (22-cm capillar}' array, Applied Biosystems) under CE injection conditions of 6 kV and 65 sec and run for 650 seconds at 30° C. The identification and quantification of the released VeraTagSup®/Sup tag was carried out as described above for the DTT-release assay.

Example 7. VeraTag® Assay Formats—Antibody Combinations

1. DTT-Release Assays

For the experiments shown in FIGS. 2A-2B and FIG. 8A, the PD-L1 VeraTag® assay was conducted using (1) rabbit anti-human PD-L1 monoclonal antibody E1L3N at 0.6

µg/mL and (2) goat anti-rabbit secondary antibody conjugated to VeraTag® reporter molecule Pro125 at 0.4 µg/mL. The molecular tag was released via reduction using DTT. An exemplary schematic of this assay format is shown in FIG. 1E.

For the experiments shown in FIGS. 5A, 5B, 5C, 6A, and 8B, the PD1 VeraTag® assay was conducted using (1) mouse anti-human monoclonal antibody NAT105 (Cell Marque) or EH33 (Cell Signaling Technologies) or J121 (eBioscience) at the concentrations indicated in the figures and (2) 1 ug/mL goat anti-mouse IgG (Jackson ImmunoResearch Laboratories Inc., catalog number 115-005-146) conjugated to Pro125 VeraTag® reporter. The molecular tag was released via reduction using DTT. An exemplary schematic of this assay format is shown in FIG. 1E.

2. Light-Release Assays

Figure 6A:
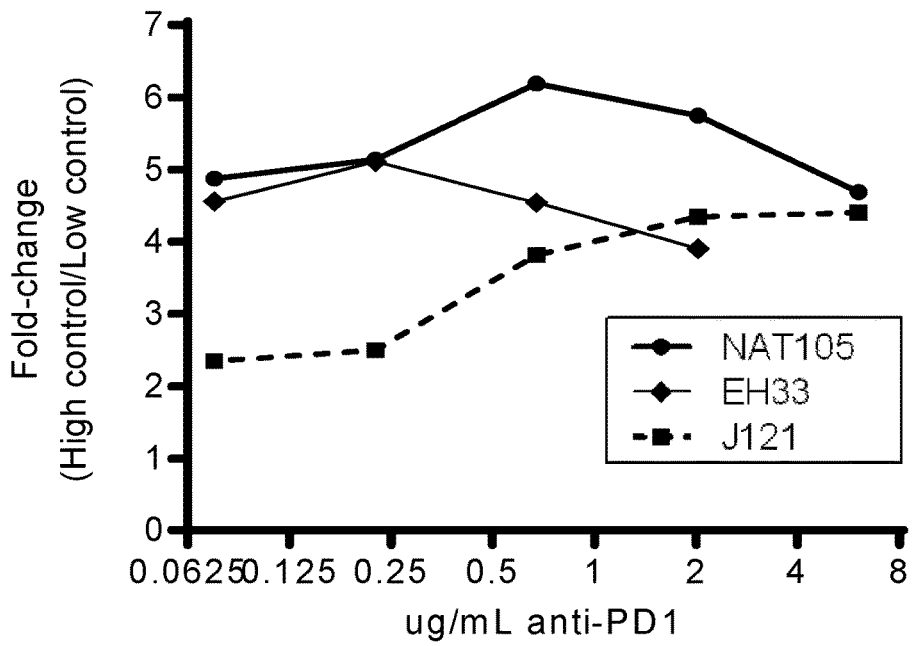
FIG. 6A shows the fold-change in PD-1 detected by VeraTag® assay (RPA) between the 500,000 or 25,000 Jurkat cell experiments as described in FIG. 5A-5C according to some aspects of the disclosure. The X-axis shows the antibody concentration and the y-axis shows the fold-change in the amount of PD-1 detected by the VeraTag® assay (RPA).
Figure 6B:
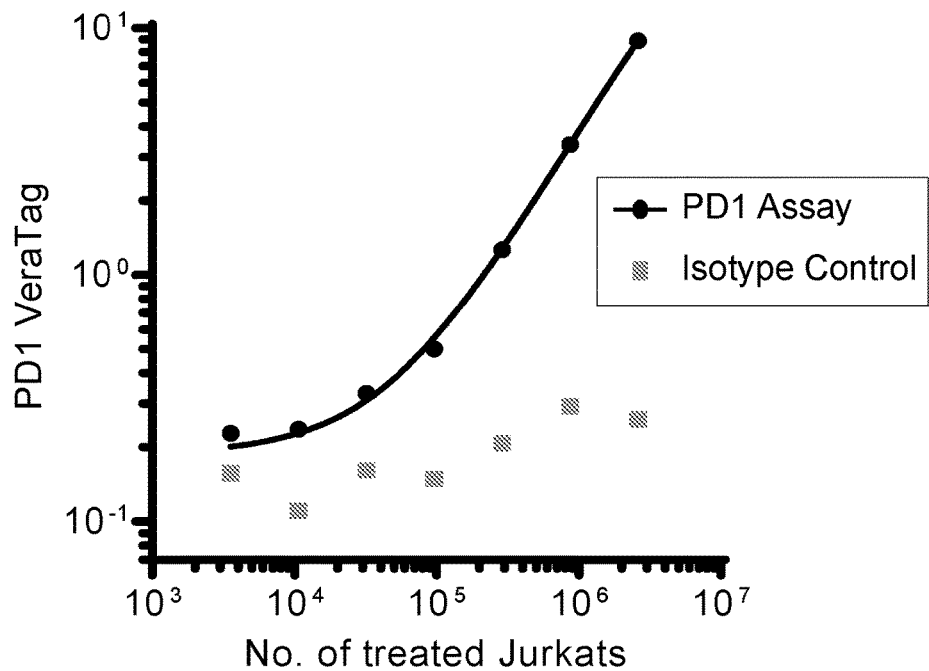
FIG. 6B shows a graph illustrating the relationship between the number of PHA-stimulated Jurkat cells and the amount of PD-1 detectable by VeraTag® assay according to some aspects of the disclosure. The assay format used mouse anti-human PD-1 monoclonal antibody NAT105, goat anti-mouse IgG1 (conjugated to biotin), and goat anti-human PD-1 monoclonal antibody AF1086 (tag labeled) in a proximity-based, light release assay as shown schematically in FIG. 1D. An increasing amount of PD-1 as detected by VeraTag® assay (y-axis) was observed with increasing amounts of stimulated Jurkat cells (x-axis). In contrast, replacing the mouse anti-human PD-1 monoclonal antibody NAT105 with a mouse IgG1 isotype control resulted in very little signal change with increasing amounts of stimulated Jurkat cells, indicating that the signal detected was PD-1 specific (not due to antibody background binding alone).
Figure 9A:
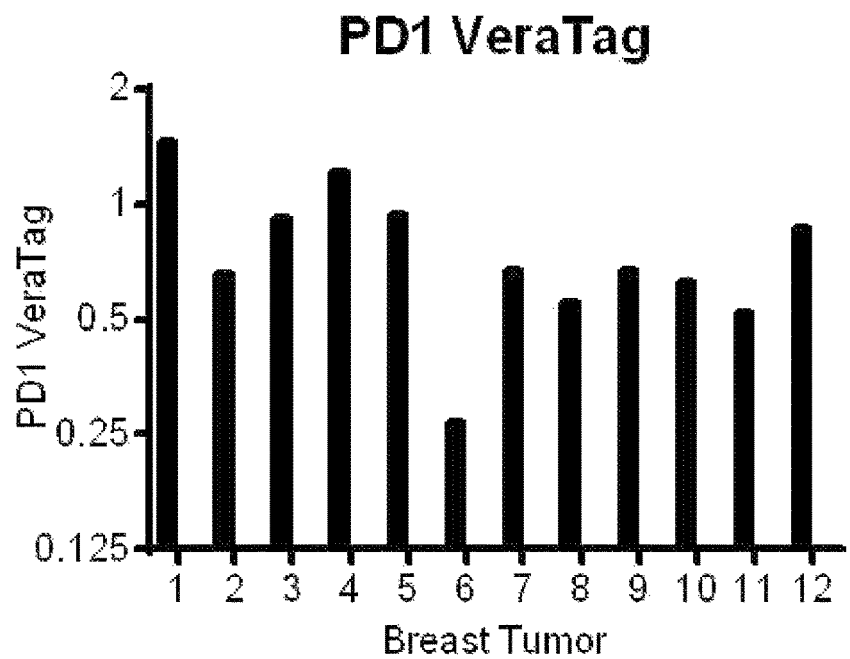
FIG. 9A shows analysis of PD-1 protein levels by VeraTag® assay in 12 human breast cancer tumors (Asterand Bioscience) pre-selected for the presence of tumor infiltrating lymphocytes (TILs) according to some aspects of the disclosure. The VeraTag® assay format used is a proximity-based, light release assay as shown in FIG. 1D, and employed mouse anti-human PD-1 monoclonal antibody NAT105, goat anti-mouse IgG1 (conjugated to biotin), and goat anti-human PD-1 monoclonal antibody AF1086 conjugated to a tag. X-axis: tumor sample; y-axis: VeraTag® assay signal (RPA). Some samples were also analyzed for PD-L1 protein expression using the VeraTag® assay (as shown in FIG. 2B).

For the experiments shown in FIG. 6B and FIG. 9A, the PD-1 antibody VeraTag® assay was conducted using (1) mouse anti-human PD-1 monoclonal antibody NAT105 (Cell Marque) at 1 µg/mL, (2) goat anti-mouse IgG1 secondary antibody (Rockland Immunochemicals Inc.) conjugated to biotin at 1 µg/mL, and (3) goat anti-human PD-1 AF1086 (R&D Systems) conjugated to VeraTag® reporter molecule Pro11 at 1 µg/mL. The molecular tag was release via light. An exemplary schematic of this assay format is shown in FIG. 1D.

For the experiments shown in FIG. 8C, the PD-1-PD-L1 complex VeraTag® assay was conducted using (1) mouse anti-human PD-1 monoclonal antibody NAT105 (Cell Marque) at 1 µg/mL, (2) rabbit anti-human PD-L1 monoclonal antibody E1L3N (Cell Signaling Technologies) at 0.5 µg/mL, (3) goat anti-mouse secondary antibody (Jackson ImmunoResearch Labs) conjugated to VeraTag® reporter molecule Pro11 at 1 µg/mL, and (4) goat anti-rabbit secondary antibody (Southern Biotech) conjugated to biotin at 0.6 µg/mL. The molecular tag was released via light. An exemplary schematic of this assay format is shown in FIG. 1I.

Figure 8D:
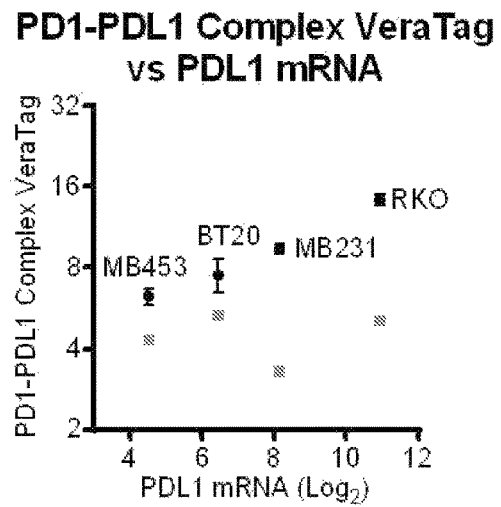
FIG. 8D shows a plot demonstrating a correlation between PD-L1 mRNA and the amount of PD-1-PD-L1 complex as measured by VeraTag® assay following co-culturing of four cancer cell lines with Jurkat cells according to some aspects of the disclosure. The cancer cell lines assessed were MDA-MB-435, BT20, MB-231, and RKO, which have increasing levels of PD-L1 mRNA expression and relatively similar levels of PD-1 mRNA expression as shown in FIG. 2A (bottom). The mRNA expression levels were obtained from the CCLE database. The amount of PD-1-PD-L1 complex was measured using a VeraTag® assay as shown in FIG. 1H employing rabbit anti-human PD-L1 antibody E1L3N, goat anti-human PD-1 antibody conjugated to a tag, and goat anti-rabbit IgG conjugated to biotin. As the amount of PD-L1 expression increased, the amount of PD-1-PD-L1 complex detected using the VeraTag® assay increased as well (black circles with deviation bars). Parallel experiments conducted by replacing the rabbit anti-human PDL1 antibody E1L3N with rabbit IgG (an isotype control) resulted in very little signal change with increasing amounts of PD-L1 expression, reflecting the background signal in the assay (grey squares).
Figure 9B:
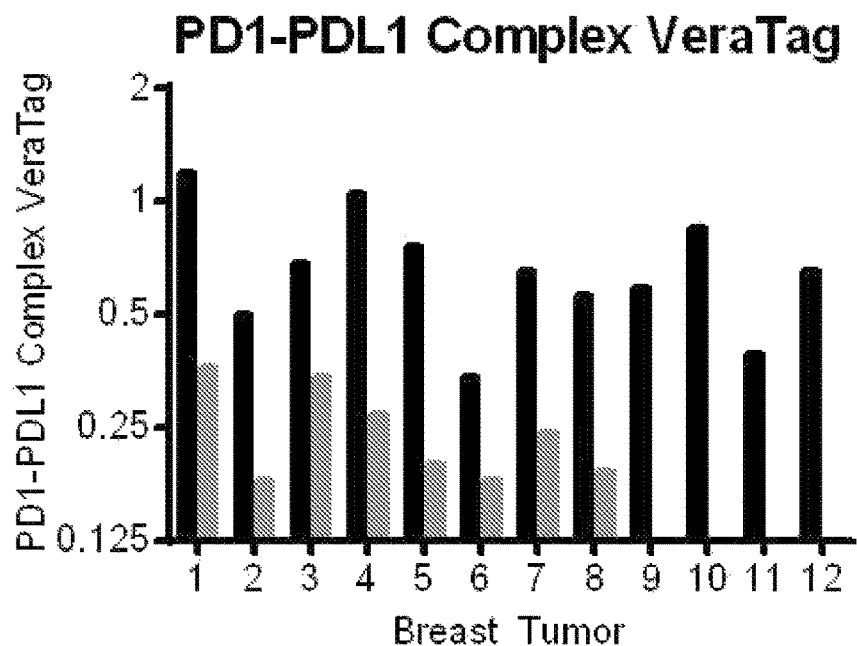
FIG. 9B shows analysis of PD-1-PD-L1 complex levels by VeraTag® assay in the same 12 human breast cancer tumors as assessed in FIG. 9A according to some aspects of the disclosure. The VeraTag® assay format used is a proximity-based, light release assay as shown in FIG. 1H, and employed rabbit anti-human PD-L1 antibody E1L3N, goat anti-rabbit IgG conjugated to biotin, and goat anti-human PD-1 antibody AF1086 conjugated to a tag. X-axis: tumor sample; y-axis: VeraTag® assay signal (RPA). The black bars are the amount of complex detected, while the grey bars show the amount of background detected in parallel VeraTag® assays using a control isotype antibody.

For the experiments shown in FIG. 8D and FIG. 9B, the PD-1-PD-L1 complex VeraTag® assay was conducted using (1) goat anti-human PD-1 polyclonal antibody AF1086 (R&D Systems) at 1 µg/mL conjugated to VeraTag® reporter molecule Pro11, (2) rabbit anti-human PD-L1 monoclonal antibody E1L3N (Cell Signaling Technologies) at 0.6 µg/mL, (3) goat anti-rabbit IgG secondary antibody (Rockland Immunochemicals Inc.) conjugated to biotin at 1 µg/mL. The molecular tag was released via light. An exemplary schematic of this assay format is shown in FIG. 1H. An isotype control assay was carried out by replacing the rabbit monoclonal antibody E1L3N with an equal amount of rabbit IgG.

Example 8. Expression of PD1 and PDL1mRNA from CCLE Database

FIG. 2A top shows the mRNA expression levels of PD1 and PDL1 from 1,036 cancer cell lines available from CCLE plotted. The data is available from the Cancer Cell Line Encyclopedia (CCLE, data available at www.broadinstitute.org/ccle/home). PD-L1 mRNA levels show a dynamic range of ~250-fold, while PD-1 mRNA levels are much less variable, having a dynamic range of approximately 5-fold.

FIG. 2A bottom shows the relationship between the mRNA expression levels of PD1 and PDL1 from the same CCLE data set as in FIG. 2A top plotted against each other and with the four adherent cell lines (MB453, BT20, MB231 and RKO) and the Jurkat suspension cell line plotted as well (labeled and identified as stars). These adherent cell lines were chosen to represent the wide dynamic range of PD-L1 mRNA expression, reflective of the entire CCLE population of cell lines.

The expression of PDL1 protein as determined by VeraTag® assay was also compared to PDL1 mRNA expression level in breast cancer, NSCLC, and SCCHN as obtained from public databases TCGA and CCLE. The PD-L1 VeraTag® assay was performed on FFPE breast, NSCLC and SCCHN blocks obtained from Asterand Biosciences as described above and the tumor area normalized PD-1 VeraTag® signal (RF/mm$^2$) was plotted for each sample from each cancer type. Significant Mann-Whitney p-values ($p<0.001$, GraphPad Prism 6) were suggestive of differences in the PD-L1 protein levels from breast compared to either NSCLC or SCCHN (FIG. 2B, left panel). The PD-L1 protein levels from VeraTag® are compared to the mRNA levels available from either TCGA (FIG. 2B, center panel) or CCLE (FIG. 2B, right panel) from the same cancer types. Consistent with the differences observed in PDL1 protein levels between cancer types, the mRNA levels also demonstrated similar differences.

Example 9. Assessing PD-1 Protein Levels in Cell Lines Using the VeraTag® Assay

The monoclonal antibodies recognizing human PD-1 tested are set forth above in Table 2. A goat anti-mouse secondary antibody was purchased from Jackson ImmunoResearch Labs.

Comparison of pH 6.2 and at pH 9.0 HIER buffer with a selection of anti-human PD-1 antibodies on 500,000 or 25,000 stimulated Jurkat cells are shown in FIG. 3, and are compared against a control (secondary antibody-only). Anti-PD-1 antibody 12A7D7 produced a very strong signal in all conditions tested, suggestive of a significant amount of non-specific binding to the fixed samples, with the remainder of anti-PD-1 antibodies demonstrating varying amounts of differences in signal between the two cell amounts and HIER buffers. FIG. 4 transforms the results from FIG. 3 to fold-change in RPA as the ratio of the 500,000 cells/25,000 cells for each HIER buffer. Anti-PD-1 antibodies NAT105, J121, and EH33 in HIER pH 6.2 buffer demonstrated the largest fold-change, suggesting that these antibodies had the greatest sensitivity for PD-1 in the assay when used with HIER pH 6.2 buffer.

Another experiment was conducted in which anti-PD-1 antibodies NAT105 (FIG. 5A), EH33 (FIG. 5B) and J121 (FIG. 5C) were titrated in the VeraTag® assay, thus expanding on the results shown in FIG. 3. The experimental results shown in FIGS. 5A-5C expand on those shown in FIG. 3 as the experiment included a titration of the NAT105 (FIG. 5A), EH33 (FIG. 5B) and J121 (FIG. 5C) anti-PD-1 antibodies. A comparison of the fold-change is shown in FIG. 6A. As described above, HIER pH 6.2 buffer was used on 500,000 and 25,000 fixed, stimulated Jurkat cells/slide, and the VeraTag® assay was performed using a goat anti-mouse-Pro125 antibody. Anti-PD-1 antibodies NAT105 and EH33 showed similar RPAs throughout the antibody titration from the 500,000 cells sample, while antibodies NAT105 and J121 had similar RPAs from the 25,000 cells sample. This is also reflected in the fold-change (FIG. 6A), with NAT105 having the largest fold-change throughout the antibody titration, suggesting this antibody has the best sensitivity for PD-1.

An additional experiment was conducted to measure PD-1 protein levels in increasing numbers of stimulated Jurkat cells using a different VeraTag® assay format using the methods described above. In this experiment, the assay format involved proximity-dependent, light-release of VeraTag® reporter molecule Pro11 conjugated to a goat anti-human PD-1 antibody AF1086 (R&D Systems) paired with a mouse anti-human PD-1 antibody NAT105 (Cell Marque) and a goat anti-mouse secondary antibody (Rockland Immunochemicals Inc.) conjugated to biotin. An exemplary schematic of this assay format is shown in FIG. 1D.

FIG. 6B shows an increasing amount of PHA-stimulated and fixed Jurkat cells were assayed using the PD1 VeraTag® assay. There was a liner increase in PD1 VeraTag® signal observed with increasing amounts of Jurkat cells. In contrast, replacing the mouse anti-human PD1 monoclonal antibody NAT105 with a mouse IgG1 isotype control resulted in very little signal change with increasing amounts of stimulated Jurkat cells, indicating that the signal detected was PD1 specific and not entirely due to antibody background binding.

Example 10. Assaying Co-Cultures for PD1, PDL1 and the PD1-PDL1 Complex Using the VeraTag® Assay Fixed samples produced from co-culturing MD-MB231 or RKO adherent cell lines with the Jurkat suspension cell line were analyzed with VeraTag® assays for detection of PD-L1 (FIG. 8A), PD-1 (FIG. 8B), and PD-1-PD-L1 complex (FIG. 8C). The PD-L1 VeraTag® assay was performed with rabbit anti-human PD-L1 monoclonal antibody E1L3N (Cell Signaling Technologies) and a goat anti-rabbit secondary antibody-Pro125 VeraTag® conjugate as described above (DTT-release PDL-1 VeraTag® assay, see schematic in FIG. 1E). In fixed co-cultures of MDA-MB231-Jurkats and RKO-Jurkats, the VeraTag® PD-L1 signal could potentially originate from either cell line in the culture. There was an approximate 16-fold difference in PD-L1 VeraTag® signal between the MDA-MB231-Jurkat and RKO-Jurkat co-cultures, consistent with the different mRNA expression levels from the individual MDA-MB231 and RKO cell lines as shown in Table 3 below. Furthermore, a similar PD-L1 VeraTag® signal was seen with increasing amounts of Jurkat cells (co-culture conditions 1× vs 5×), suggesting that the added Jurkats were a minimal contributor to the overall PD-L1 VeraTag® signal and consistent with their low mRNA expression level (see Table 3). Taken together, it is likely that the majority of the PD-L1 VeraTag® signal from these co-cultures originated from either the MDA-MB231 or RKO adherent cell lines.

TABLE 3

Cell lines tested

| Cell Line Name | Cancer Type | Culture Properties | PD-1 mRNA Expression ($\log_2$) | PD-L1 mRNA Expression ($\log_2$) |
| --- | --- | --- | --- | --- |
| Jurkat | T-cell | Suspension | 4.03 | 5.20 |
| MDA-MB453 | Breast | Adherent | 4.41 | 4.50 |
| BT-20 | Breast | Adherent | 4.59 | 6.45 |
| MDA-MB231 | Breast | Adherent | 4.40 | 8.16 |
| RKO | Large Intestine | Adherent | 4.54 | 10.94 |

FIG. 8B shows the results from the PD-1 VeraTag® assay of the co-culture experiment. A larger PD-1 VeraTag® signal was observed in both the RKO-Jurkat co-culture conditions than the MDA-MB231-Jurkat co-culture. Both adherent cell lines and the Jurkat cell line express very low amounts of PD-1 mRNA (see Table 3), and previous work has shown that PD-1 protein expression can be induced on Jurkat cells by stimulation with PHA (Vibhakar. R., et al., Activation-induced expression of human programmed death-1 gene in T-lymphocytes, *Exp. Cell Res.* 232(1):25-28 (1997)). The larger PD-1 VeraTag® signal in the RKO-Jukat co-cultures is consistent with the idea that the amount of PD-1 expressing Jurkat cells that are fixed following co-culturing is proportional to the PD-L1 expression level of the adherent cell line. FIG. 8B also shows an increase in the PD-1 VeraTag® signal with increasing amounts of Jurkat T-cells (co-culture conditions 1× and 5× Jurkats) in both the MDA-MB231- and RKO-Jurkat co-cultures, suggesting that that amount of PD-1 expressing Jurkat cells that are fixed following co-culturing is also reflective of the amount of PD-1.

FIG. 8C shows the results from the PD-1-PD-L1 complex VeraTag® assay of the co-culture experiment. The PD-1-PD-L1 complex VeraTag® assay employs the proximity-dependent, light-release of VeraTag® reporter molecule Pro11 as shown schematically in FIG. 1I. The PD-1-PD-L1 complex VeraTag® assay results from the MDA-MB-231 and RKO cell lines-co-cultured with Jurkat cells in FIG. 8C track with the PD-1 VeraTag® assay results in FIG. 8B. The amount of PD-1-PD-L1 protein complex as measured by VeraTag® assay was increased with increased PD-L1 expression (RKO-Jurkat co-culture), and the amount of PD-1-PD-L1 complex increased with increased PD-1 expression (condition 1× vs 5×). A possible limitation of this fixed, co-cultured model system is the requirement for the Jurkat cells to be interacting with the adherent cells in order for them to be present in the final fixed preparation. It is anticipated that a survey of FFPE breast, NSCLC and SCCHN tumor samples will provide a more thorough understanding of the relationships between these three VeraTag® assays (PD-L1, PD-1 and PD-1-PD-L1 complex).

An additional experiment was conducted to measure the PD1-PD-L1 complex with a different VeraTag® assay format (schematically shown in FIG. 1H). As shown in FIG. 8D, the amount of PD1-PD-L1 complex in the MDA-MB-453, BT20, MDA-MB-231, and RKO cell lines-co-cultured with Jurkat cells track with the PD-L1 mRNA from CCLE. The amount of PD-1-PD-L1 protein complex as measured by VeraTag® assay increased as PD-L1 mRNA expression increased, In contrast, replacing the rabbit anti-human PD-L1 monoclonal antibody E1L3N with a rabbit IgG isotype control antibody resulted in minimal PD1-PD-L1 complex VeraTag® signal change with increasing amounts of PD-L1 mRNA (grey squares, isotype control). As stated above, a possible limitation of this fixed, co-cultured model system is the requirement for the Jurkat cells to be interacting with the adherent cells in order for them to be present in the final fixed preparation, and since the adherent cell lines used in this study have increasing amounts of PD-L1 expression we anticipated increasing amount of PD1-PD-L1 complex.

Example 11. Detection and Quantification of PD-1, PD-L1, and PD-1/PD-L1 Complex in Human Breast Cancer Tumors The amount of PD1 and PD1-PDL1 complex was measured by VeraTag® assay in 12 human breast cancer tumors (Asterand Bioscience). Samples were pre-selected for the presence of tumor infiltrating lymphocytes (TILs) prior to the VeraTag® assay by pathological examination of an adjacent H&E stained slide. In addition, a select set of samples were subjected to immunohistochemical staining for PD1 using mouse anti-human PD1 monoclonal antibody NAT105 and rabbit anti-human PDL1 monoclonal antibody E1L3N, which confirmed tumor cell membrane expression on TILs of PD1 and PDL1, respectively (data not shown). The PD1 VeraTag® assay format used was the proximity-based, light release assay as shown in FIG. 1D, and described above with respect to FIG. 6B. The PD1-PDL1 complex VeraTag® assay format used was a proximity-based, light release assay as shown schematically in FIG. 1H and described above with respect to FIG. 8D. For the PD1-PDL1 complex VeraTag® assay, background signal was assessed in parallel using the isotype control assay format as described above with respect to FIG. 8D.

The amount of PD-1 protein expression is shown in FIG. 9A, The amount of PD1-PDL1 complex detected is shown in FIG. 9B (black bars). For the isotype control assay results (grey bars), a minimum assay signal-to-background ratio of 2 was considered acceptable, and all samples passed. There was a general trend for the assay signal-to-background ratio to increase as the assay signal increased.

FIGS. 10A-10C show all pair-wise comparisons between the amounts of PD1, PDL1 and PD1-PDL1 complex as detected using the VeraTag® assay from the breast cancer samples. Pearson correlation coefficients ($R^2$) and p-values for each comparison are shown to the right of the graphs. The data plotted was that from FIG. 9A (PD-1), FIG. 9B (PD1-PDL1 complex), and FIG. 2B, left panel (PD-L1; 8 of the 12 breast cancer samples). The strongest correlation was observed between PD1 and PD1:PD-L1 complex (Pearson $R^2=0.7638$), suggesting that PD1, and not PD-L1, may be the primary driver for complex formation.

All patents, patent publications, patent applications, journal articles, books, technical references, and the like discussed in the instant disclosure are incorporated herein by reference in their entirety for all purposes.

It is to be understood that the figures and descriptions of the invention have been simplified to illustrate elements that are relevant for a clear understanding of the invention. It should be appreciated that the figures are presented for illustrative purposes and not as construction drawings. Omitted details and modifications or alternative embodiments are within the purview of persons of ordinary skill in the art.

It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

What is claimed is:

1. A method of quantifying a protein-protein interaction between two cells in a sample, the method comprising:
    (a) providing a sample comprising a first cell and a second cell, wherein the first cell expresses a first protein on its cell surface and wherein the second cell expresses a second protein on its cell surface;
    (b) providing a first antibody binding composition specific for the first protein;
    (c) providing a second antibody binding composition specific for the second protein;
    (d) providing a third antibody composition that is capable of specifically binding to the first antibody composition, the third antibody composition comprising a molecular tag attached thereto via a cleavable linkage;
    (e) providing a fourth antibody composition that is capable of specifically binding to the second antibody composition, the fourth antibody composition comprising a cleavage inducing moiety attached thereto;
    (f) contacting the sample with the first antibody binding composition, the second antibody binding composition, the third antibody binding composition, and the fourth antibody binding composition;
        wherein the third antibody binding composition binds to the first antibody binding composition, and wherein the fourth antibody binding composition binds to the second antibody binding composition,
    (g) washing the sample that has been contacted with the first, second, third, and fourth antibody binding compositions,
    (h) after the wash step in (f), inducing cleavage of the molecular tag from the third antibody binding composition, when the third antibody binding composition is within an effective proximity range of the cleavage inducing moiety attached to the fourth antibody binding composition, thereby releasing the molecular tag; and
    (I) detecting the amount of released molecular tag as a measure of the amount of protein-protein interaction between the first protein and the second protein.

2. The method of claim 1, wherein the first cell is a T cell and the second cell is a tumor cell.

3. The method of claim 1, wherein the first protein is Programmed death 1 (PD-1) and the second protein is Programmed death ligand 1 (PD-L1).

4. The method of claim 1, wherein the cleavage of the molecular tag by the cleavage inducing moiety is induced by light.

5. The method of claim 1, wherein the sample is a tissue sample, cultured cells, or peripheral blood mononuclear cells (PMBCs).

6. The method of claim 1, wherein the sample is a cancer biopsy sample.

7. The method of claim 1, wherein the sample is a formalin-fixed paraffin-embedded (FFPE) sample.

8. The method of claim 1, wherein the sample is a blood sample.

9. A method of screening test agents for the ability to disrupt or promote formation of a protein-protein interaction between two cells in a sample, the method comprising:
(a) contacting a test cell culture with a test agent, the test cell culture comprising a first cell expressing a first protein on its cell surface and a second cell expressing a second protein on its cell surface;
(b) measuring the amount of protein-protein interaction between the first protein and the second protein using the method of claim 1; and
(c) selecting the test agent based on the amount of protein-protein interaction as compared to the amount of protein-protein interaction measured between the first protein and the second protein in a control cell culture not contacted with the test agent, the control cell culture comprising the first cell expressing the first protein on its cell surface and the second cell expressing the second protein on its cell surface.

10. The method of claim 9, wherein the test agent is an inhibitor of the protein-protein interaction between the first protein and the second protein if the amount of protein-protein interaction is decreased in the test cell culture as compared to the control cell culture.

11. The method of claim 9, wherein the test agent is a promoter of the protein-protein interaction between the first protein and the second protein if the amount of protein-protein interaction is increased in the test cell culture as compared to the control cell culture.

12. The method of claim 9, wherein the first cell and the second cell are different cell types.

13. The method of claim 9, wherein the first cell and the second cell are different cancer cell lines.

14. The method of claim 9, wherein one of the first cell and the second cell is an adherent cell and the other is a non-adherent cell.

15. The method of claim 9, wherein the first cell is a Jurkat cell and the second cell is an adherent cancer cell.

16. The method of claim 1, wherein one of the first cell and the second cell is an adherent cell and the other is a non-adherent cell.

17. The method of claim 9, wherein the first protein is PD-1 and the second protein is PD-L1.

* * * * *